United States Patent [19]

Posner et al.

[11] Patent Number: 5,225,437
[45] Date of Patent: Jul. 6, 1993

[54] 1,2,4-TRIOXANE COMPOUNDS HAVING ANTIMALARIAL ACTIVITY

[75] Inventors: Gary Posner; Chang H. Oh, both of Baltimore, Md.

[73] Assignee: The Johns Hopkins University, Baltimore, Md.

[21] Appl. No.: 823,960

[22] Filed: Jan. 23, 1992

[51] Int. Cl.$^5$ .................. A61K 31/335; C07D 321/10; C07D 323/06
[52] U.S. Cl. .................................... 514/450; 548/249; 549/349; 549/351; 549/354; 549/355; 549/367; 549/368
[58] Field of Search ............... 549/349, 351, 354, 355, 549/367, 368; 514/450; 548/249

[56] References Cited

PUBLICATIONS

Posner et al, "Tetrahedron Letters", vol. 32, No. 34, pp. 4235–4238, 1991.

*Primary Examiner*—C. Warren Ivy
*Assistant Examiner*—Ba K. Trinh
*Attorney, Agent, or Firm*—Cushman, Darby & Cushman

[57] ABSTRACT

Novel 1,2,4-trioxanes which possess anti-malarial activity.

9 Claims, No Drawings

1,2,4-TRIOXANE COMPOUNDS HAVING ANTIMALARIAL ACTIVITY

BACKGROUND OF THE INVENTION

1. Field of the Invention

The present invention relates to a novel group of 1,2,4-trioxane compounds which demonstrate useful anti-malarial activity.

2. Background of the Invention

Because of the widespread incidence of malaria in certain parts of the world and because of the increasing parasite resistance to standard anti-malarial drugs, there is an urgent need for new and effective anti-malarial drugs.

A wide variety of anti-malarial compounds have been proposed for use. One such compound is qinghaosu (also called QHS or antemisinin). See Klayman, *Science* (1985) 228 1049–1055. This compound is a sesquiterpene lactone which bears a peroxide group and, unlike most other anti-malarials, lacks a nitrogen-containing heterocyclic ring system.

QHS has been determined to have the following structure:

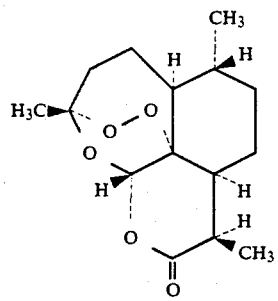

Derivatives of QHS such as dihydroqinghaosu, artemether and the water-soluble sodium artesunate, have also been disclosed as having anti-malarial properties.

Certain synthetic 1,2,4-trioxane derivatives have also been described as having anti-malarial activity. For example, Jefford has shown that a tricyclic 1,2,4-trioxane can be prepared from a keto vinyl ether using $^1O_2$ to obtain a structurally simplified and yet active synthetic version of the naturally-occurring anti-malarial antemisinin. See *Tetrahedron Letters*, 1989, 30, 4485.

Further disclosures by Jefford and others relating to 1,2,4-trioxane derivatives and their use as antimalarials include WO 88/04660, EPA 0286316, EPA 0335717, EPA 0290959 and EPA 0330520.

BRIEF DESCRIPTION OF THE INVENTION

The invention provides a group of novel 1,2,4-trioxanes which have been found to possess unexpectedly greater anti-malarial activity than, for example, QHS and other closely related compounds. The anti-malarial 1,2,4-trioxanes of the invention can be structurally represented by the following formula (I):

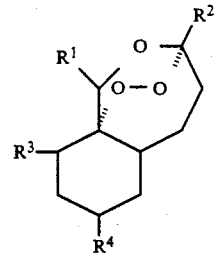

(I)

and the optical stereoisomers (enantiomers) thereof wherein:

$R^1$ is lower alkoxy, aryloxy or aralkoxy (e.g., phenoxy or benzyloxy);

$R^2$ is lower alkyl, hydroxy substituted-lower alkyl or ester or ether derivatives of such hydroxy substituted-lower alkyl;

$R^3$ is —$(CH_2)_mQ$ where Q is halogen or —$OR^5$ where $R^5$ is hydrogen, lower alkyl, lower alkenyl, lower alkynyl, cycloalkyl, aryl, or alkyl or heteroaralkyl, or $R^5$ os

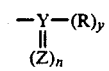

where

Y is C, S or P;

Z is O or S;

R is hydrogen, lower alkyl, lower alkenyl, lower alkynyl, cycloalkyl, lower alkoxy, aryloxy, aryl, aralkyl, mono- and di-lower alkyl amino or mono- or di-aryl amino;

n is 1 or 2;

y is 1 or 2; and m is 1, 2, 3, or 4; and $R^4$ is hydrogen or one or two lower alkyl.

References to "lower alkyl", "lower alkoxy", "lower alkenyl" and "lower alkynyl" in the above represent alkyl, alkoxy, alkenyl or alkynyl of 1–6 carbon atoms while representative aryl, aryloxy, or aralkyl include phenyl or naphthyl, phenoxy or aralkoxy, naphthoxy, benzyloxy or benzyl. These substituents may be substituted by lower alkyl, lower alkoxy, halogen, hydroxy, nitro, carboxylate ester groups or the like. Similarly, the alkyl, alkoxy, alkenyl and alkynyl may be substituted by, for example, one or more halogen, hydroxy or nitro groups.

Examples of cycloalkyl substituents include cycloalkyl of 3 to 7 carbons, i.e. cyclopropyl to cycloheptyl.

Heteroaralkyl include any such substituents where the hetero atom is, for example, O, N or S. Representative examples are pyrimidyl, pyridyl, thiophenyl, furanyl and the like.

Typical alkenyl and alkynyl include, for example, ethenyl, propenyl, ethynyl and propynyl.

One preferred subgroup of compounds of Formula I includes those wherein $R^1$ is methoxy, $R^2$ is methyl, $R^4$ is hydrogen, and $R^3$ is —$(CH_2)_mQ$ where m is 2 and Q is —$OR^5$ and $R^5$ is

where R is hydrogen, lower alkyl or aryl, substituted or unsubstituted or mono- or di-lower alkyl amino or mono- or di-aryl amino. As noted above, substitution in the aryl group can include lower alkyl, lower alkoxy, halogen, hydroxy, nitro, carboxylate ester groups or the like. This group includes carbamates where R is, for example, dialkylamino, i.e. —N(alkyl)$_2$ or diarylamino, i.e. —N(Ar)$_2$.

Other preferred subgroups comprise compounds where m, $R^1$, $R^2$, $R^3$ and $R^4$ have the meanings given in the preceding paragraph and $R^5$ is either

or

where R is alkyl, aryl, alkoxy or aryloxy.

As will be appreciated, the invention contemplates alcohol (when $R^5$ is hydrogen), ethers (when $R^5$ is, for example, lower alkyl, alkenyl, aryl, aralkyl or heteroaralkyl) and esters (where $R^5$ is

namely, the carboxylate, sulfamate, carbamate, phosphate or sulfonate esters.

As indicated, the compounds of the invention include the stereoisomers of the 1,2,4-trioxanes. A preferred group of such stereoisomers may be represented by the following:

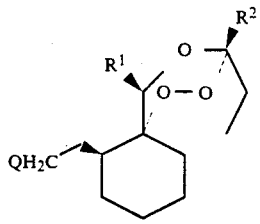

(II)

where $R^1$ is methoxy, $R^2$ is methyl and Q is as defined above.

The esters represent a particularly important category of compounds within the invention. Representative of such esters are those listed in Table I, these being prepared from trioxane alcohol as shown:

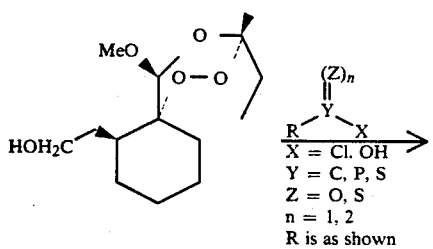

X = Cl, OH
Y = C, P, S
Z = O, S
n = 1, 2
R is as shown

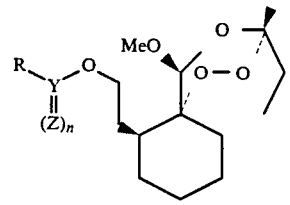

TABLE I

| Compound No. | Z | n | Y | R |
|---|---|---|---|---|
| 18 | O | 1 | C | HOOC—C$_6$H$_4$— |
| 19 | O | 1 | C | MeOOC—C$_6$H$_4$— |
| 20 | O | 1 | C | Me$_2$NCH$_2$CH$_2$OOC—C$_6$H$_4$— |
| 21 | O | 1 | C | Et$_2$N—C(O)—C$_6$H$_4$— |
| 22 | O | 1 | C | Trioxane-OOC—C$_6$H$_4$— |
| 23 | O | 2 | S | H$_3$C—C$_6$H$_4$— |
| 24 | O | 2 | S | 2-COOMe-C$_6$H$_4$— |
| 25 | O | 1 | C | t-Bu-O-C(O)-N(H)-Et |
| 26 | O | 1 | C | Me$_2$N— |
| 27 | O | 2 | S | Me$_2$N— |
| 28 | O | 1 | P | (CH$_3$CH$_2$O)$_2$— |
| 31 | O | 1 | C | Ph$_2$N— |
| 32 | O | 2 | S | 5-Me$_2$N-naphthyl |
| 33 | O | 1 | P | (PhO)$_2$— |
| 34 | O | 1 | C | Et$_2$N— |
| 35 | S | 1 | P | (EtO)$_2$— |

TABLE I-continued

| Compound No. | Z | n | Y | R |
|---|---|---|---|---|
| 36 | O | 1 | C | NaOOC—C₆H₄— |

Of the above group of compounds, it is noted that the carboxylate esters (19) and (21) are comparable in potency to artemether which is one of the most clinically effective anti-malarial drugs, and have considerably higher potency than the clinically used Chinese drug, artemisinin. Other particularly potent 1,2,4-trioxanes include the carbamate esters (26), (31) and (34) and the phosphate esters (28) and (33).

Representative 1,2,4-trioxane ethers according to the invention are shown in Table II, these being prepared by the following reaction:

TABLE II

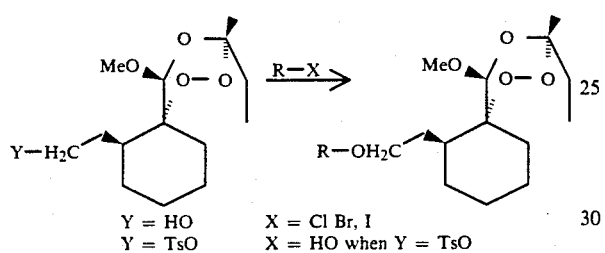

| Compound No. | R |
|---|---|
| 101 | Me— |
| 102 | PhCH₂— |
| 103 | (EtO)₂P(O)—CH₂— |
| 104 | CH₂=CH—CH₂— |
| 105 | 3,5-dimethylisoxazol-4-ylmethyl |
| 106 | HOOCCH₂— |
| 107 | NaOOCCH₂— |

Of the compounds shown in Table II, ethers (102), (104) and (105) have been found to have particularly potent anti-malarial activity as disclosed herinafter.

The compounds of the invention may be synthesized in a variety of different ways. However, a representative reaction scheme for the preparation of the esters, ethers or trioxane salts is shown below:

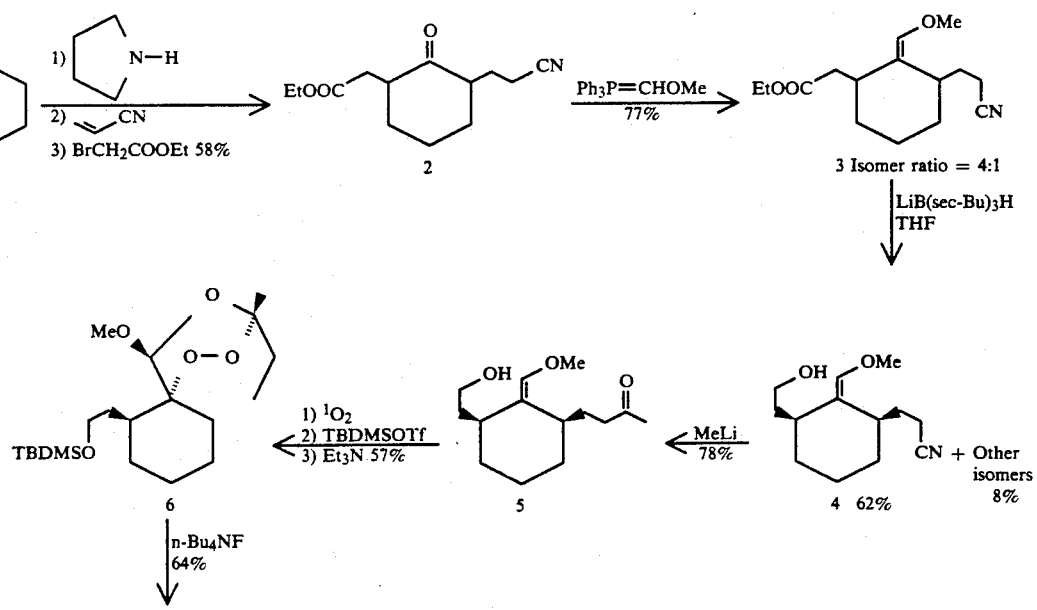

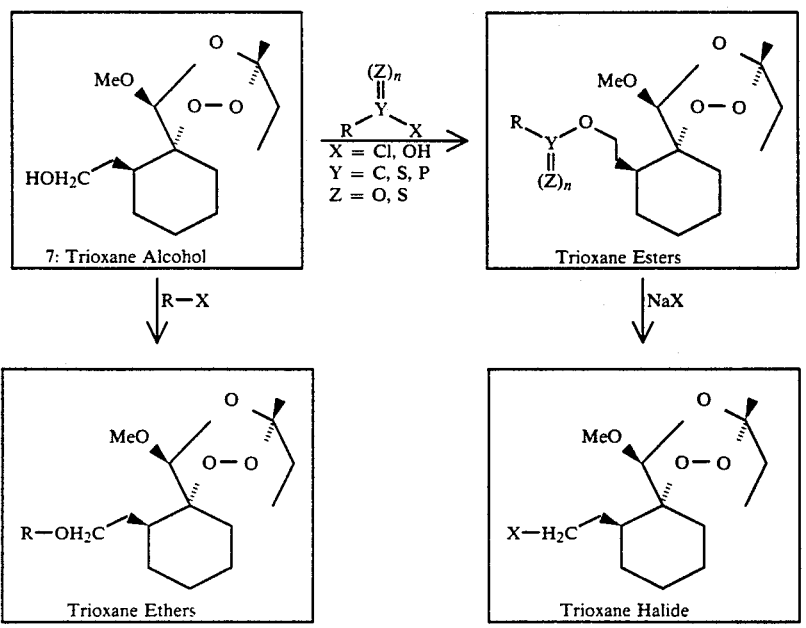
Specific examples of the preparation of compounds according to the invention is schematically shown below:
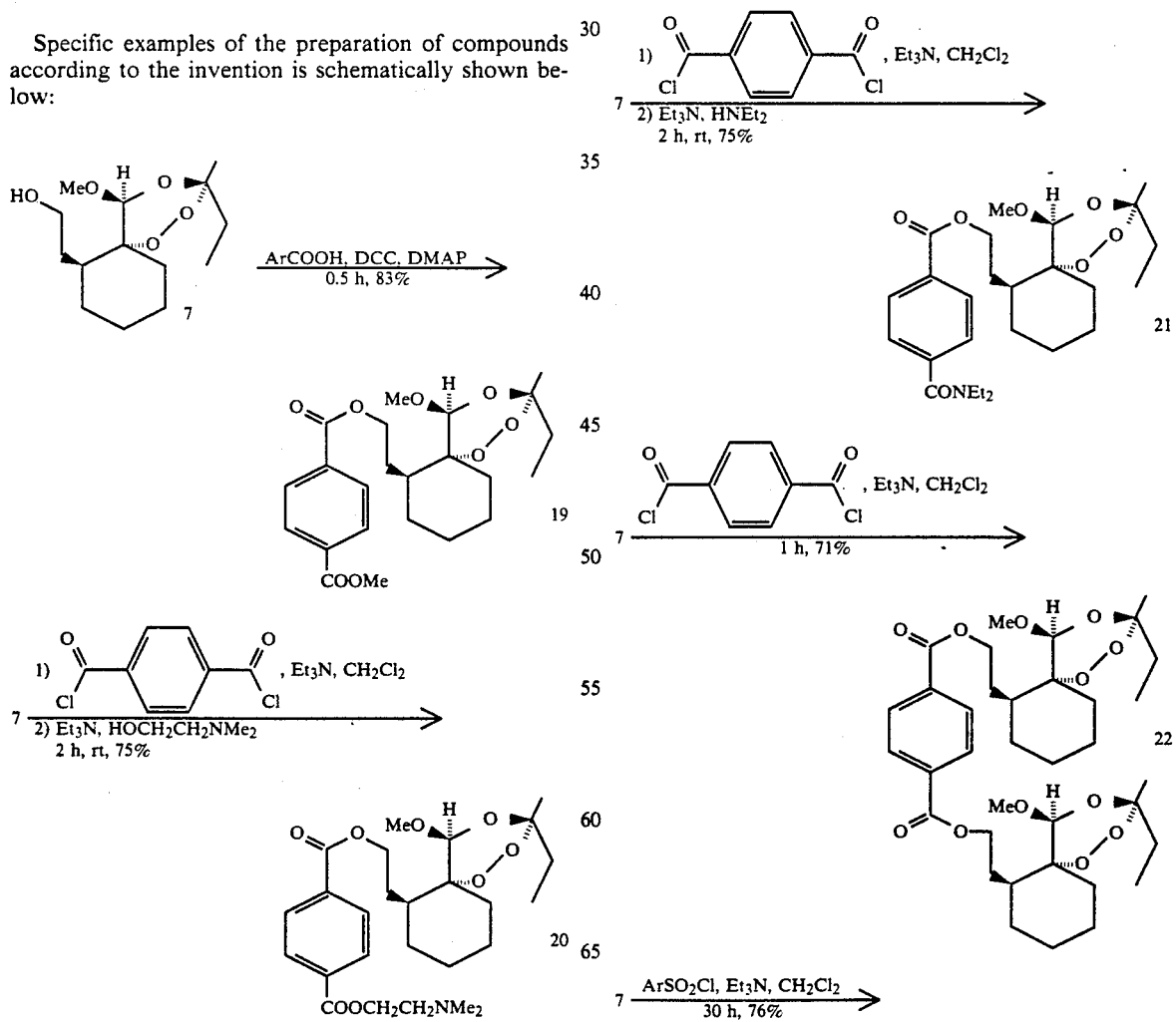

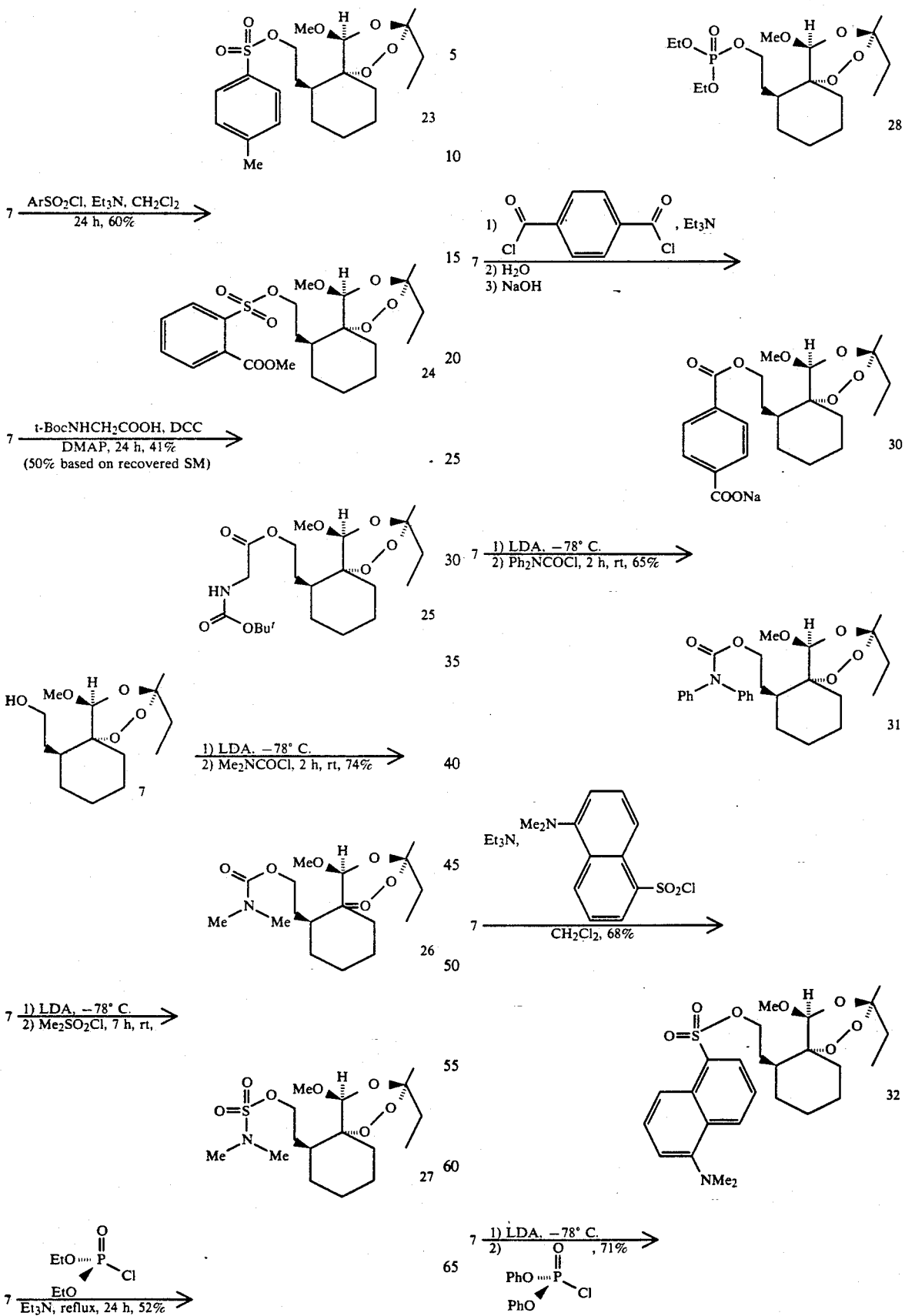

-continued
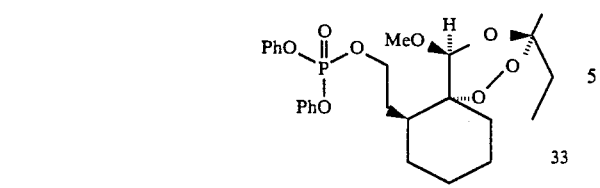
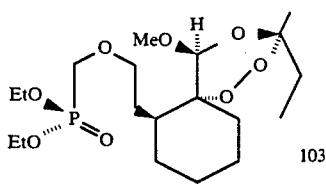
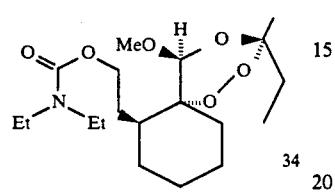
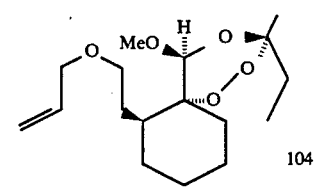
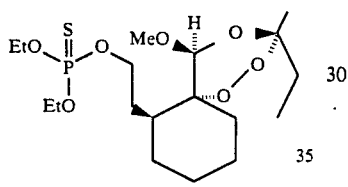
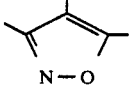
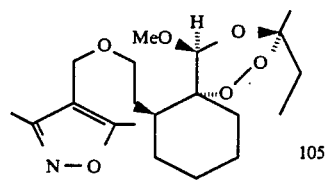
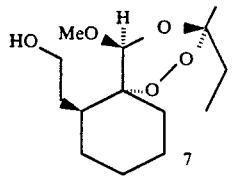
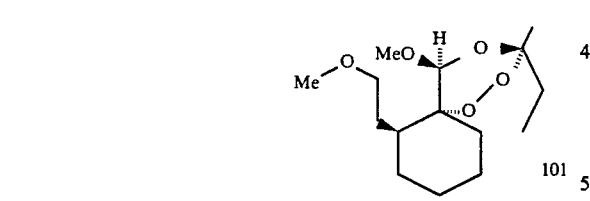
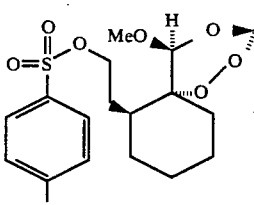
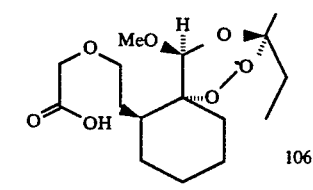
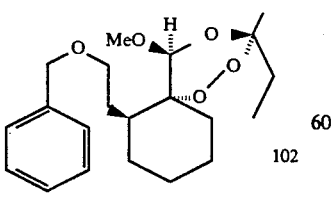
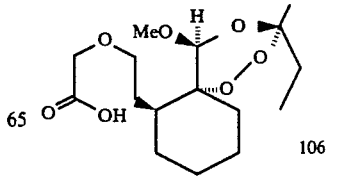

-continued

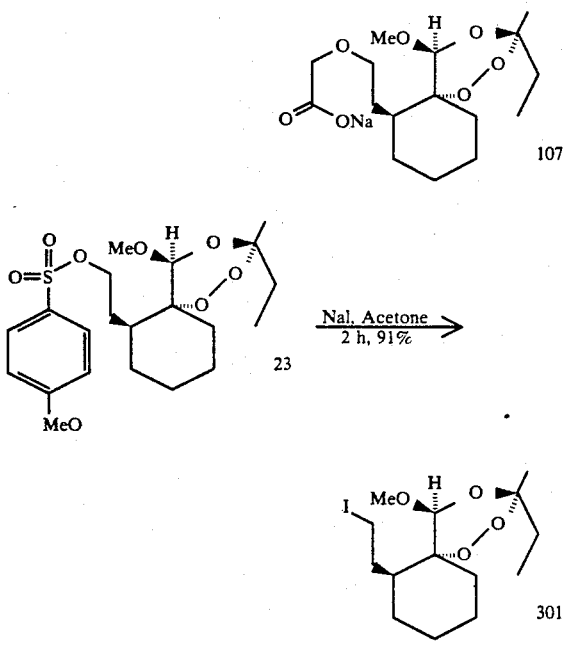

Abbreviations used in the foregoing are more fully identified below:
DCC=dicyclohexylcarbodiimide
DMAP=4-dimethylaminopyridine
LDA=lithium diisopropylamide
THF=tetrahydrofuran

DETAILED DESCRIPTION OF THE INVENTION

The invention is further illustrated by the following examples:

Preparation of 2-(2-Cyanoethyl)-6-ethoxycarbonylmethylcyclohexanone (2)

An oven dried 250 ml 1-necked round bottomed flask was charged with cyclohexanone (26.37 g, 0.27 mol) and dry benzene (50 ml). To this solution was added pyrrolidine (29 ml, 0.35 mol) over 10 min through a dropping funnel. The resultant solution was refluxed for 3 hours with azeotroping off water and then concentrated by distilling off benzene. The remaining crude enamine was dissolved in p-dioxane (100 ml) and treated with acrylonitrile (20 ml, 0.3 mol) and refluxed for 6 hours, and then slowly treated with ethyl bromoacetate (31 ml, 0.28 mol), and refluxed for further 12 hours. Then the reaction mixture was concentrated under reduced pressure, and treated with water (30 ml) and 10% sulfuric acid (50 ml) at room temperature. The resultant solution was diluted with ether (200 ml). The organic layer was separated from the aqueous layer and further extracted twice with ether (100 ml×2), combined, and washed with saturated NaCl solution (200 ml). The resulting organic layer was dried over anhydrous magnesium sulfate, and filtered, and the solvent was removed at reduced pressure to yield a crude product. Vacuum distillation at 0.1 torr afforded the desired product 2 (37.10 g, 58%) as a mixture of cis and trans stereoisomers: bp 160°–175° C. (0.1 torr); FT-IR (neat, cm$^{-1}$) 2936, 2861, 2245, 1732, 1710, 1449, 1376, 1344, 1276, 1234, 1188, 1116, 1071, 1028, 989, 947, 862, 838, 748; $^1$H NMR (CDCl$_3$, 400 MHz) δ 4.14 (q, J=7.1 Hz, 2H), 2.92 (m, 1H), 2.75 (dd, 16.6, 7.2 Hz, 1H), 2.56 (m, 1H), 2.45 (t, J=7.4 Hz, 1H), 2.43 (t, J=7.5 Hz, 1H), 2.17 (dd, J=16.6, 5.7 Hz, 2H), 2.22–2.05 (m, 2H), 1.96–1.78 (m, 2H), 1.55 (ddd, J=17.4, 8.8, 4.7 Hz, 1H), 1.42 (m, 2H), 1.26 (t, J=7.2 Hz, 3H); $^{13}$C NMR (CDCl$_3$, 100 MHz) δ 210.92, 172.22, 119.63, 48.92, 48.81, 47.35 (47.14 for minor), 34.80, 34.55, 34.25, 34.13, 4.93, 15.09 (14.07 for minor); MS (El, 70 eV, rel. intensity) 237 (M, 17), 208(12), 192(B), 191(59), 163(27), 150(58), 141(35), 95(20), 84(27), 67(13), 55(20), 49(14); HRMS (El) calcd. for C$_{13}$H$_{19}$NO$_3$ 237.1365. Found 237.1361.

EXAMPLE 2

Preparation of Vinyl Ether (3)

An oven dried 500 ml 1-necked round bottomed flask with magnetic stirring bar, serum cap, and gas-needle inlet was charged with methoxymethyl triphenylphosphonium chloride (12.30 g, 35.8 mmol) and dry THF (120 ml) and then cooled to 0° C. To this solution was added a 1.8M phenyllithium solution (21 ml, 37.8 mmol) in cyclohexane/ether over 10 min. The resultant red ylide solution was then warmed to room temperature and stirred for 3 hours and cooled to −78° C. To this ylide solution was added via cannular cyclohexanone 2 (5.68 g, 23.9 mmol) in THF (30 ml) over 10 min. After being stirred for one hour at −78° C., the reaction mixture was warmed to room temperature over 2 hours, stirred for 10 hours at room temperature, cooled to 0° C., quenched with water (50 ml), and diluted with ether (50 ml). The organic layer was separated from the aqueous layer and further extracted with ether (50 ml×2), combined and washed with saturated NaCl solution (50 ml). The combined organic layer was dried over anhydrous magnesium sulfate, and filtered, and the solvent was removed at reduced pressure to yield a crude product. Vacuum distillation at 0.05 torr gave impure product 3 (8.96 g, 77% based on 55% pure SM). Chromatography of crude product on silica gel (10:90=hexane: ethyl acetate) afforded the pure colorless oil 3 as a 4:1 mixture of stereoisomers: FT-IR (neat, cm$^{-1}$) 2931, 2857, 2244, 1732, 1662, 1454, 1369, 1278, 1247, 1210, 1174, 1129, 1111, 1038, 856, 634; $^1$H NMR (CDCl$_3$, 400 MHz) δ Major: 5.93 (s, 1H), 4.14 (q, J=7.1 Hz, 2H), 3.52 (s, 3H), 2.82 (m, 1H), 2.65 (m, 1H), 2.42 (d, J=1.9 Hz, 1H), 2.40 (d, J=1.7 Hz, 1H), 2.46–2.24 (m, 2H), 1.97–1.82 (m, 1H), 1.80–1.65 (m, 1H), 1.65–1.46 (m, 6H), 1.28 (t, J=7.1 Hz, 3H); Minor 5.85 (s, 1H), 4.11 (q, J=7.1 Hz, 2H), 3.55 (s, 3H), 3.31 (m, 1H), 2.46–2.24 (m, 4H), 2.22–1.96 (m, 1H), 1.97–1.82 (m, 1H), 1.80–1.65 (m, 1H), 1.65–1.46 (m, 1H), 1.26 (t, J=7.1 Hz, 3H); $^{13}$C NMR (CDCl$_3$, 100 MHz) δ Major: 172.44, 144.17, 120.50, 116.29, 60.19, 59.29, 40.89, 34.79, 32.49, 31.16, 30.92, 30.13, 17.80, 14.23; Minor 172.54, 143.68, 120.00, 115.15, 60.19, 59.45, 39.48, 36.68, 32.07, 31.95, 30.86, 30.01, 15.46, 14.11; MS (El, 70 eV, rel. intensity) 265 (M, 16), 250(4), 233(18), 191(33), 178(97), 137(34), 123(28), 105(B), 88(24), 75(15), 67(8); HRMS (El) calcd. for C$_{15}$H$_{23}$NO$_3$ 265.1678. Found 265.1682.

EXAMPLE 3

Preparation of Alcohol (4)

An oven dried 250 ml 1-necked bottomed flask with magnetic stirring bar, serum cap, and gas-needle inlet was charged with the above stereoisomeric mixture of 3 (8.96 g, 55% pure, 18.6 mmmol) and dry THF (100 ml), and cooled to 0° C. by means of an ice bath. To this solution was added via a gas-tight syringe a 1M THF solution of lithium trisec-butylborohydride (L-selectride, 50 ml, 50 mmol) over 20 min. After being stirred for 10 min at 0° C., the reaction mixture was slowly warmed to room temperature, stirred for 2 hours, and cooled to 0° C. This reaction mixture was quenched with water (50 ml) and concentrated to about 100 ml at reduced pressure (30 torr). The resulting solution was then cooled to 0° C., and then diluted with water (50 ml) and ether (50 ml). The organic layer was separated and the aqueous layer was acidified with 20% sulfuric acid solution (20 ml), and extracted two times with ethyl ether (50 ml×2). The combined organic layer was washed with saturated NaCl solution (100 ml), dried over anhydrous magnesium sulfate, and filtered, and the solvent was removed at reduced pressure to yield a crude product. Chromatography of the crude product on silica gel (50:50=hexane: ethyl acetate) afforded the colorless oil 4 (2.57 g, 62%) as a single stereoisomer and an inseparable mixture of stereoisomers of 4 (320 mg, 8%). 4:FT-IR (CHCl$_3$, 3408, 2930, 2864, 2245, 1660, 1453, 1241, 1209, 1130, 1114, 1057, 849, 729, 639, 561; $^1$H NMR (CDCl$_3$, 400 MHz) δ 5.90 (s, 1H), 3.64 (m, 2H), 3.54 (s, 3H), 2.83 (m, 1H), 2.33 (t, J=7.7 Hz, 2H), 2.20 (m, 1H), 1.94-1.84 (m, 1H), 1.80-1.71 (m, 1H), 1.70-1.62 (m, 2H), 1.62-1.52 (m, 6H), 1.47-1.41 (m, 1H); $^1$C NMR (CDCl$_3$, 100 MHz) δ 143.42, 120.54, 118.14, 61,36, 59.33, 38.03, 34.07, 32.89, 31.91, 31.21, 30.71, 17.96, 15.63; MS (El, 70 eV, rel. intensity) 223(10), 178(B), 137(14), 119(16); HRMS (El) calcd. for C$_{13}$H$_{21}$NO$_2$ 223.1572. Found 223.1575.

EXAMPLE 4

Preparation of Methyl Ketone (5)

An oven dried 50 ml 1-necked round bottomed flask with magnetic stirring bar, serum cap, and gas-needle inlet was charged with 4 (532.4 mg, 2.38 mmol) and dry ethyl ether (10 ml), and cooled to −78° C. by means of Dry Ice acetone bath. To this solution was added via a gas-tight syringe a 1.3M methyllithium solution (10 ml, 13.0 mmol) in ethyl ether over 2 min. After being stirred for 10 min at −78° C., the reaction mixture was slowly warmed to room temperature over 30 min, and stirred for 15 hours. This reaction mixture was quenched with water (10 ml) at 0° C., and then diluted with water (10 ml) and ether (20 ml). The organic layer was separated and the aqueous layer was extracted two times with ethyl ether (20 ml×2). The combined organic layer was washed with saturated NaCl solution (20 ml), dried over anhydrous magnesium sulfate, and filtered, and the solvent was removed at reduced pressure to yield a crude product. Chromatography on silica gel (50:50=hexane: ethyl acetate) afforded the colorless oil 5 (444.0 mg, 78%): FT-IR (CHCl$_3$), 3417, 2928, 2863, 1713, 1661, 1453, 1362, 1242, 1210, 1168, 1128, 1114, 1088, 1057, 1013, 925, 885, 848, 642, 557; $^1$H NMR (CDCl$_3$, 400 MHz) δ 5.85 (s, 1H), 3.63 (m, 2H), 3.51 (s, 3H), 2.75 (q, J=6.2 Hz, 1H), 2.51 (m, J=5.6 Hz, 1H), 2.36 (m, J=5.6 Hz, 1H), 2.19 (q, J=6.2 Hz, 1H), 2.13 (s, 3H), 1.74-1.65 (m, 4H), 1.65-1.38 (m, 6H), 1.27 (t, J=5.3 Hz, 1H, —O—H); $^{13}$C NMR (CDCl$_3$, 100 MHz) δ 209.83, 142.76, 119.57, 61.50, 59.15, 42.23, 38.00, 34.11, 32.18, 32.07, 31.29, 29.85, 28.37, 17.48; MS (El, 70 eV, rel intensity) 240(2), 222(1), 208(2), 182(63), 150(13), 137(68), 119(22), 108(13), 105(61), 93(46), 91(30), 79(22), 67(16), 45(43), 43(B), 41(33), 39(15); HRMS (El) calcd. for C$_{14}$H$_{24}$O$_3$ 240.1725. Found 240.1729.

EXAMPLE 5

Preparation of Trioxane Silyl Ether (6)

An oven dried 250 ml 3-necked round bottomed flask, fitted with magnetic stirring bar, serum cap, gas-needle inlet and outlet, was charged with 5 (3.03 g, 12.6 mmol), methylene blue (10 mg), and dry methylene chloride (120 ml), and cooled to −78° C. by means of Dry Ice acetone bath. Dry oxygen (flow rate: ca 1 ml/sec) was slowly bubbled to this solution for 2 hours under UV irradiation using medium pressure mercury lamp as an UV source. The resultant solution, after being vigorously stirred for 10 min, was slowly added pre-cooled t-butyldimethylsilyl trifluoromethanesulfonate (TBDMSOTf) (8 ml, 34.5 mmol) in methylene chloride (10 ml) via cannular over 5 min. The resultant solution was stirred at −78° C. for 2 hours, treated with triethylamione (12 ml), and then slowly warmed to room temperature over 4 hours. The reaction mixture was concentrated to about 20 ml under reduced pressure. The separation of the crude product with ethyl acetate and hexane (5:95) gave pure 1,2,4-trioxane 6 (2.80 g, 57%): $^1$H NMR (CDCl$_3$, 400 MHz) δ 5.15 (d, J=1.2 Hz, 1H), 3.65 (m, 2H), 3.50 (s, 3H), 2.32 (td, J=13.8, 3.6 Hz, 1H), 2.14 (q, J=8.4 Hz, 1H), 2.00 (ddd, J=14.4, 4.2, 2.5 Hz, 1H), 1.89-1.46 (m, 5H), 1.38 (s, 3H), 1.34-1.16 (m, 4H), 0.90 (s, 9H), 0.06 (s, 6H); $^{13}$C NMR (CDCl$_3$, 100 MHz) δ 105.10, 100.42, 85.30, 62.30, 56.72, 48.58, 42.03, 37.50, 32.99, 31.11, 29.46, 27.18, 25.99, 25.27, 5.27.

EXAMPLE 6

Preparation of Trioxane Alcohol (7)

To the silyl protected trioxane 6 (2.80 g, 7.2 mmol) in dry THF (10 ml) was added a 1 M THF solution of tetrabutylammonium fluoride (20 ml, 20 mmol) at 0° C. under argon atmosphere. The resulting solution was stirred for 4 hours at room temperature, and then cooled to 0° C. and diluted with water (30 ml) and ether (30 ml). The organic layer was separated and the aqueous layer was extracted two times with ethyl ether (20 ml×2). The combined organic layer was washed with saturated NaCl solution (30 ml), dried over anhydrous magnesium sulfate, and filtered, and the solvent was removed at reduced pressure to yield a crude product. Chromatography on silica gel (80:20=hexane:ethyl acetate) gave the corresponding trioxane alcohol 7 (1.255 g, 64%) as a colorless solid. Recrystallization of compound 7 from hexane furnished a needle type crystal: mp 83°-4° C.; FT-IR (CHCl$_3$) 3617, 3013, 2934, 2862, 1443, 1408, 1376, 1224, 1218, 1211, 1077, 1042, 1009, 963, 950, 909, 897, 871; $^1$H NMR (CDCl$_3$, 400 Mhz) δ 5.19 (d, J=1.6 Hz, 1H), 3.78 (m, 1H), 3.66 (m, 1H), 3.50 (s, 3H), 2.32 (ddd, J=14.0, 13.8, 3.5 Hz, 1H), 2.08-1.95 (m, 2H), 1.90-1.78 (m, 1H), 1.75 (dd, J=6.0 Hz, 5.5 Hz, 2H), 1.70-1.51 (m, 6H), 1.46-1.35 (m, 2H), 1.38 (s, 3H), 1.30-1.20 (m, 1H); $^{13}$C NMR (CDCl$_3$, 100 Mhz) δ 105.27, 100.18, 85.58, 61.60, 56.70, 48.61, 41.70, 37.49, 33.91, 31.08, 30.13, 27.09, 25.61, 25.24; MS (Cl, NH$_3$, rel. intensity) 290 (M+18, 51), 273 (1), 258 (23), 241 (18), 223 (57), 205 (15), 195 (B), 181 (62), 169 (8), 150 (13), 137 (82). HRMS (Cl, NH$_3$) calcd for C$_{14}$H$_{28}$NO$_3$ (M+18) 290.1967. Found 290.1962. Anal calcd for C$_{14}$H$_{24}$O$_5$: C, 61.74; H, 8.88. Found: C, 61.58; H. 8.83.

EXAMPLE 7

Preparation of Trioxane Carboxylate Ester (18)

An oven dried 50 ml 1-necked round bottomed flask with magnetic stirring bar, serum cap, and gas-needle inlet was charged with terephthaloyl chloride (494.0 mg, 2.4 mmol) and dry methylene chloride (5 ml), and cooled to 0° C. by means of ice bath. This solution was treated with triethylamine (1.9 ml, 13.6 mmol) via a gas-tight syringe, stirred for 10 min at 0° C., slowly warmed to room temperature and stirred for 2 hours. To this solution was added via cannular trioxane alcohol 7 (176.9 mg, 0.65 mmol) in methylene chloride (10 ml), at −78° C. After being stirred for 10 min at −78° C., the reaction mixture was slowly warmed to room temperature over 1 hour, stirred for additional two hours. Then the reaction mixture was cooled to 0° C., quenched with water (10 ml), and then acidified with saturated sodium bisulfate (10 ml). The aqueous layer was extracted three times with ethyl acetate (20 ml×3). The combined organic layer was washed with saturated NaCl solution (20 ml), dried over anhydrous magnesium sulfate, and filtered, and the solvent was removed at reduced pressure to yield a crude product which was directly separated by silica gel column chromatography to afford the corresponding trioxane carboxylic acid 18 (78.0 mg, 13%) as white solid whose $^1$H NMR was essentially identical with that of recrystallized trioxane 18. Recrystallization from ether/hexane afforded pure trioxane 18 as white solid: mp 168°–170° C.; FT-IR (CHCl$_3$) 3695, 3519, 2932, 2861, 1719, 1701, 1602, 1578, 1506, 1377, 1275, 1210, 1121, 1018, 1009; $^1$H NMR (CDCl$_3$, 400 MHz) δ 8.17 (d, J=8.8 Hz, 2H), 8.15 (d, J=8.8 Hz, 2H), 5.21 (s, 1H), 4.49-4.36 (m, 2H), 3.53 (s, 3H), 2.45-2.30 (m, 2H), 2.26-2.00 (m, 1H), 1.88-1.66 (m, 6H), 1.65-1.51 (m, 4H), 1.40 (s, 3H), 1.29-1.23 (m, 1H); $^{13}$C NMR (CDCl$_3$, 100 MHz) δ 170.69, 165.69, 134.95, 132.88, 130.15, 129.66, 105.31, 100.09, 85.20, 64.49, 56.70, 48.56, 42.30, 37.47, 30.99, 29.43, 29.18, 27.09, 25.92, 25.17; LRMS (Cl, NH$_3$, rel. intensity) 438 (M+18, 18), 403 (M-17, 2), 389(7), 378(36), 361(19), 343(65), 223(19), 195(B), 176(6), 149(13), 137(9). HRMS (Cl, NH$_3$ calcd. for C$_{22}$H$_{32}$NO$_8$ 438.2128. Found 438.2136. Anal Calcd for C$_{22}$H$_{28}$O$_8$: C, 62.84; H, 6.71. Found: C, 62.64; H, 6.67.

EXAMPLE 8

Preparation of Trioxane Carboxylate Ester (19)

An oven dried 10 ml 1-necked round bottomed flask with magnetic stirring bar, serum cap, and gas-needle inlet was charged with monomethly terephthalate (38.5 mg, 0.2 mmol), N,N-dimethylaminopyridine (46.1 mg), dicyclohexylcarbodiimide (54.5 mg, 0.26 mmol), and added methylene chloride (2 ml) via gas-tight syringe at 0° C. under argon atmosphere. After being stirred for 10 min at 0° C., the reaction mixture was slowly warmed to room temperature, and stirred for 30 min and cooled to 0° C. To this solution was added via cannular trioxane alcohol 7 (23.7 mg, 0.1 mmol) in methylene chloride (1 ml) via cannular. After being stirred for 10 min at 0° C., the reaction mixture was slowly warmed to room temperature and stirred for additional 30 min and the solvent was removed at reduced pressure to yield a crude product which was directly separated by silica gel column chromatography to afford the corresponding pure trioxane carboxylate ester 19 (30.5 mg, 83%) as colorless oil; FT-IR (neat) 2929, 2861, 1722, 1437, 1409, 1272, 1209, 1118, 1007, 963, 897, 873, 731, 666; $^1$H NMR (CDCl$_3$, 400 MHz) δ 8.10 (s, 4H), 5.21 (s, 1H), 4.45–4.37 (m, 2H), 3.95 (s, 3H), 3.52 (s, 3H), 2.45–2.30 (m, 2H), 2.06–2.00 (m, 1H), 1.89–1.50 (m, 9H), 1.44–1.35 (m, 1H), 1.39 (s, 3H), 1.32–1.20 (m, 1H); $^{13}$C NMR (CDCl$_3$, 100 MHz) δ 166.34, 165.80, 134.17, 133.80, 129.56, 105.29, 100.09, 85.19, 64.41, 56.70, 52.42, 48.56, 42.30, 37.47, 30.99, 29.42, 29.18, 27.09, 25.92, 25.17.

EXAMPLE 9

Preparation of Trioxane Carboxylate Ester (20)

An oven dried 10 ml 1-necked round bottomed flask with magnetic stirring bar, serum cap, and gas-needle inlet was charged with terephthaloyl chloride (64.5 mg, 0.3 mmol) and dry methylene chloride (1 ml), and cooled to 0° C. by means of ice bath. To this solution was added via a gas-tight syringe triethylamine (45 μl, 03 mmol). After the reaction mixture was stirred at room temperature for 0.5 hour, cooled to 0° C., and treated with trioxane alcohol 7 (41.9 mg, 0.15 mmol) in methylene chloride (1 ml) via cannular. This solution was stirred for two hours at room temperature, and then treated with triethylamine (100 μl) and N,N-dimethylethanolamine (100 μl) at 0° C., and then slowly warmed to room temperature. This reaction mixture was stirred for additional two hours and the solvent was removed at reduced pressure to yield a crude product which was directly separated by silica gel column chromatography to afford the corresponding pure trioxane carboxylate ester 20 (51.5 mg, 68%) as a colorless oil: FT-IR (neat) 2935, 2860, 28.25, 1721, 1578, 1458, 1408, 1374, 1270, 1209, 1120, 1008, 731; $^1$H NMR (CDCl$_3$, 400 MHz) δ 8.10 (s, 4H), 5.21 (s, 1H), 4.46 (t, J=5.8 Hz, 2H), 4.45–4.35 (m, 2H), 3.52 (s, 3H), 2.73 (t, J=5.8 Hz, 2H), 2.35 (s, 6H), 2.38–2.32 (m, 1H), 2.07–1.95 (m, 2H), 1.91–1.50 (m, 9H), 1.44–1.36 (m, 1H), 1.39 (s, 3H), 1.30–1.20 (m, 1H); $^{13}$C NMR (CDCl$_3$, 100 MHz) δ 165.83, 165.79, 134.17, 133.86, 129.59, 129.53, 105.27, 100.08, 85.17, 64.39, 63.37, 57.75, 56.69, 48.55, 45.83, 42.30, 37.46, 30.97, 29.41, 29.16, 27.08, 25.92, 25.16; LRMS (CI, NH$_3$, rel. intensity) 492 (M+H, 51), 462 (7), 433 (27), 432 (B), 71 (14), 58 (29). HRMS (CI, NH$_3$) calcd for C$_{26}$H$_{37}$NO$_8$ (M+H) 492.2597. Found 492.2599.

EXAMPLE 10

Preparation of Trioxane Carboxylate Ester (21)

An oven dried 10 ml 1-necked round bottomed flask with magnetic stirring bar, serum cap, and gas-needle inlet was charged with terephthaloyl chloride (61.2 mg, 0.3 mmol) and dry methylene chloride (1 ml), and cooled to 0° C. by means of ice bath. To this solution was added via a gas-tight syringe triethylamine (45 μl, 0.3 mmol). After the reaction mixture was stirred at room temperature for 0.5 hour, cooled to 0° C., and treated with trioxane alcohol 7 (35.2 mg, 0.13 mmol) in methylene chloride (1 ml) via cannular. This solution was stirred for two hours at room temperature, and then treated with triethylamine (75 μl) and diethylamine (75 μl) at 0° C., and then slowly warmed to room temperature. This reaction mixture was stirred for additional two hours and the solvent was removed at reduced pressure to yield a crude product which was directly separated by silica gel column chromatography to afford the corresponding pure trioxane carboxylate ester 21 (51.7 mg, 84%) as a colorless oil: FT-IR (neat) 29.34, 28.58, 1719, 1636, 1569, 1508, 1459, 1439, 1376, 1274, 1210, 1120, 1007, 962, 872, 724; $^1$H NMR (CDCl$_3$, 400 MHz) δ 8.08 (dd, J=6.8, 1.6 Hz, 2H), 7.43 (dd, J=6.8, 1.6 Hz, 2H), 5.21 (s, 1H), 4.46-4.33 (m, 2H), 3.56 (q, J=6.0 Hz, 2H), 3.52 (s, 3H), 3.21 (q, J=6.0 Hz, 2H), 2.44-2.29 (m, 2H), 2.06-2.00 (m, 1H), 1.90-1.49 (m, 8H), 1.43-1.34 (m, 1H), 1.39 (s, 3H), 1.32-1.20 (m, 5H), 1.10 (t, J=6.6 Hz, 3H); $^{13}$C NMR (CDCl$_3$, 100 MHz) δ 170.30, 165.96, 141.47, 130.88, 129.79, 126.25, 105.26, 100.09, 85.20, 64.13, 56.69, 48.56, 43.20, 42.28, 39.29, 37.48, 30.99, 29.37, 29.16, 27.08, 25.91, 25.17, 14.19, 12.88.

EXAMPLE 11

Preparation of Trioxane Carboxylate Ester (22)

An oven dried 10 ml 1-necked round bottomed flask with magnetic stirring bar, serum cap, and gas-needle inlet was charged with terephthaloyl chloride (95.7 mg, 0.5 mmol) and dry methylene chloride (1 ml), and cooled to 0° C. by means of ice bath. To this solution was added via a gas-tight syringe triethylamine (200 μl, 1.4 mmol). After the reaction mixture was slowly warmed to room temperature over 0.5 hour, and stirred for 0.5 hour and treated with trioxane alcohol 7 (58.5 mg, 0.22 mmol) in methylene chloride (1 ml). This reaction mixture was stirred for an hour and the solvent was removed at reduced pressure to yield a crude product which was directly separated by silica gel column chromatography to afford the corresponding pure bistrioxane carboxylate ester 22 (51.8 mg, 71%) as a colorless oil: FT-IR (neat) 2929, 2860, 1720, 1442, 1408, 1375, 1270, 1209, 1121, 1008, 962, 899, 872, 732; $^1$H NMR (CDCl$_3$, 400 MHz) δ 8.10 (s, 4H), 5.21 (s, 2H), 4.48-4.35 (m, 4H), 3.53 (s, 6H), 2.45-2.30 (m, 4H), 2.06-2.00 (m, 2H), 1.91-1.66 (m, 4H), 1.65-1.50 (m, 14H), 1.45-1.34 (m, 2H), 1.39 (s, 6H); 1.34-1.21 (m, 2H); $^{13}$C NMR (CDCl$_3$, 100 MHz) δ 166.85, 134.08, 129.55, 105.29, 100.11, 85.19, 64.38, 56.71, 48.56, 42.33, 37.48, 31.00, 29.43, 29.18, 27.10, 25.93, 25.18; LRMS (NH,, rel. intensity) 692 (M+18, 9), 657 (1), 632 (11), 572 (64), 466 (11), 404 (12), 348 (22), 318 (17) 233 (16), 195 (B), 177 (11), 168 (24), 137 (14), 119 (35), 117 (23). HRMS (CI, NH$_3$) calcd for C$_{36}$H$_{54}$NO$_{12}$ (M+NH.) 692.3646. Found 692.3662.

EXAMPLE 12

Preparation of Trioxane Sulfonate Ester (23)

An oven dried 10 ml 1-necked round bottomed flask with magnetic stirring bar, serum cap, and gas-needle inlet was charged with p-toluenesulfonyl chloride (85.4 mg, 0.45 mmol) and dry methylene chloride (1 ml), and cooled to 0° C. by means of an ice bath. To this solution was added via a gas-tight syringe triethylamine (180 μl, 1.3 mmol). After the reaction mixture was stirred at room temperature for 0.5 hour, cooled to 0° C., and treated with trioxane alcohol 7 (100.7 mg, 0.37 mmol) in methylene chloride (1 ml) via cannular. This reaction mixture was stirred for 30 hours and the solvent was removed at reduced pressure to yield a crude product which was directly separated by silica gel column chromatography to afford the corresponding pure trioxane sulfonate ester 23 (119.4 mg, 76%) as a white solid which was spectroscopically pure. Recrystallization from ether/hexane (10:90) gave white crystals: mp 88°-89° C.; FT-IR (neat) 2929, 2860, 1598, 1442, 1361, 1209, 1189, 1177, 1120, 1097, 1008, 948, 902, 872, 815, 662; $^1$H NMR (CDCl$_3$, 400 MHz) δ 7.80 (d, J=7.8 Hz, 2H), 7.34 (d, J=7.8 Hz, 2H), 5.02 (d, J=1.6 Hz, 1H), 4.11 (m, 2H), 3.45 (s, 3H), 2.45 (s, 3H), 2.28 (m, 1H), 2.23-2.14 (m, 1H), 1.99 (m, 1H), 1.86-1.40 (m, 9H), 1.36 (s, 3H), 1.27-1.11 (m, 2H); $^{13}$C NMR (CDCl$_3$, 100 MHz) δ 144.60, 133.25, 129.80, 127.96, 105.26, 99.80, 85.00, 69.59, 56.60, 48.52, 41.80, 37.42, 30.87, 29.87, 29.57, 27.02, 25.86, 25.03, 21.61. Anal. Calcd for C$_{21}$H$_{30}$O$_7$S:C, 59.14; H, 7.08; S, 7.51. Found: C, 59.20; H, 7.03; S, 7.26.

EXAMPLE 13

Preparation of Trioxane Sulfonate Ester (24)

An oven dried 10 ml 1-necked round bottomed flask with magnetic stirring bar, serum cap, and gas-needle inlet was charged with 2-methoxycarbonylbenzenesulfonyl chloride (105.6 mg, 0.45 mmol) and dry methylene chloride (1 ml), and cooled to 0° C. by means of ice bath. To this solution was added via a gas-tight syringe triethylamine (200 μl, 1.4 mmol). After the reaction mixture was stirred at room temperature for 0.5 hour, cooled to 0° C., and treated with trioxane alcohol 7 (41.6 mg, 0.15 mmol) in methylene chloride (1 ml) via cannular. This reaction mixture was stirred for 24 hours and the solvent was removed at reduced pressure to yield a crude product which was directly separated by silica gel column chromatography to afford the corresponding pure trioxane sulfonate ester 24 (42.7 mg, 60%) as a colorless oil: FT-IR (neat) 2934, 1739, 1434, 1363, 1296, 1260, 1183, 1159, 1121, 1062, 1008, 952, 872, 831, 761, 683, 666; $^1$H NMR (CDCl$_3$, 400 MHz) δ 8.04 (dd, J=7.6, 0.8 Hz, 1H), 7.71-7.61 (m, 3H), 5.07 (d, J=1.2 Hz, 1H), 4.29-4.20 (m, 2H), 3.97 (s, 3H), 3.47 (s, 3H), 2.33-2.22 (m, 2H), 2.00 (m, 1H), 1.86-1.68 (m, 2H), 1.67-1.60 (m, 1H), 1.60-1.50 (m, 6H), 1.35 (s, 3H), 1.36-1.26 (m, 1H), 1.23-1.13 (m, 1H); $^{13}$C NMR (CDCl$_3$, 100 MHz) δ 167.29, 134.24, 133 38, 133.27, 130.76, 129.83, 129.39, 105.27, 99.85, 84.99, 70.44, 56.66, 53.27, 48.50, 41.63, 37.40, 30.85, 29.87, 29.49, 27.01, 25.87, 25.01; LRMS 488 (M+18, 34), 380 (4), 272 (B), 255 (8), 234 (32), 223 (17), 195 (81), 137 (10), HRMS (CI, NH$_3$), calcd for C$_{22}$H$_{34}$NO$_9$S (M+NH$_4$) 488.1954. Found 488.1952.

EXAMPLE 14

Preparation of Trioxane Carboxylate Ester (25)

An oven dried 10 ml 1-necked round bottomed flask with magnetic stirring bar, serum cap, and gas-needle inlet was charged with N-tertbutoxycarbonyl glycine (35.1 mg, 0.2 mmol), N,N-dimethylaminopyridine (24.9 mg), dicyclohexylcarbodiimide (42.9 mg, 0.2 mmol), and added methylene chloride (2 ml) via gas-tight syringe at 0° C. under argon atmosphere. After being stirred for 10 min at 0° C., the reaction mixture was slowly warmed to room temperature, and stirred for 30 min and cooled to 0° C. To this solution was added via cannula trioxane alcohol 7 (26.2 mg, 0.1 mmol) in methylene chloride (1 ml) at 0° C. After being stirred for 10 min at 0° C., the reaction mixture was slowly warmed to room temperature and stirred for additional 2 hours and the solvent was removed at reduced pressure to yield a crude product which was directly separated by silica gel column chromatography to afford the corresponding pure trioxane carboxylate ester 25 (18.5 mg, 50% based on recovered 7) as a colorless oil; FT-IR (CHCl$_3$) 3448, 3016, 2933, 2862, 1743, 1713, 1508, 1394, 1368, 1229, 1205, 1161, 1121, 1078, 1059, 1009, 963, 951, 909, 871, 794, 666; $^1$H NMR (CDCl$_3$, 400 MHz) δ 5.14 (d, J=1.2 Hz, 1H), 5.02 (bs, 1H), 4.29-4.16 (m, 2H), 3.91 (d, J=5.2 Hz, 1H), 3.50 (s, 3H), 2.32 (ddd, J=14.8, 14.2, 3.0 Hz, 1H), 2.28–2.19 (m, 2H), 2.05 (m, 1H), 1.90–1.72 (m, 2H), 1.72–1.50 (m, 6H), 1.47–1.36 (m, 1H), 1.46 (s, 9H), 1.38 (s, 3H), 1.32–1.20 (m, 1H); $^{13}$C NMR (CDCl$_3$, 100 MHz) δ 170.54, 155.67, 105.27, 100.04, 85.13, 80.10, 64.36, 56.68, 48.53, 42.45, 42.13, 37.45, 30.95, 29.48, 29.17, 28.30, 27.07, 25.90, 25 13.

EXAMPLE 15

Preparation of Trioxane Carbamate Ester (26)

An oven dried 10 ml 1-necked round bottomed flask with magnetic stirring bar, serum cap, and gas-needle inlet was charged with dry THF (1 ml), n-buthyllithium (1.5M in hexane, 150 μl, 0.23 mmol) and treated with dry diisopropylamine (31 μl, 0.22 mmol) at 0° C. under argon atmosphere. This LDA solution was cooled to −78° C. and treated with trioxane alcohol 7 (20.3 mg, 0.08 mmol) in dry THF (1 ml) via cannular. After the reaction mixture was stirred for 5 min at −78° C., N,N-dimethylcarbamoyl chloride (40 μl, 0.43 mmol) was added to the reaction mixture, and then slowly warmed to room temperature over 10 minutes. This reaction mixture was stirred for additional two hours and quenched with water (5 ml) at 0° C. The organic layer was extracted twice with ether (10 ml×2), combined, washed with saturated sodium chloride solution (10 ml), and dried over anhydrous magnesium sulfate, filtered, and concentrated under reduced pressure to yield a crude product which was separated by silica gel column chromatography to afford the corresponding pure trioxane carbamate ester 26 (18.9 mg, 74%) as a colorless solid: mp (hexane) 116°–116.5° C.; FT-IR (CHCl$_3$) 3019, 2933, 2862, 1687, 1497, 1444, 1408, 1376, 1224, 1206, 1008, 672; $^1$H NMR (CDCl$_3$, 400 MHz) δ 5.16 (d, J=1.2 Hz, 1H), 4.18 (ddd, J=10.8, 8.0, 4.8 Hz, 1H), 4.06 (dt, J=10.8, 7.4 Hz, 1H), 3.50 (s, 3H), 2.90 (s, 6H), 2.32 (ddd, J=14.0, 13.5, 3.5 Hz, 1H), 2.25 (m, 1H), 2.05 (ddd, J=14.0, 4.8, 2.6 Hz, 1H), 1.90–1.49 (m, 8H), 1.43–1.17 (m, 3H), 1.38 (s, 3H); $^{13}$C NMR (CDCl$_3$, 100 Mhz) δ 156.74, 105.19, 100.20, 85.21, 64.18, 56.70, 48.57, 42.20, 37.49, 36.36, 35.92, 31.05, 29.41, 29.24, 27.12, 25.95, 25.21. Anal. calcd for C$_{17}$H$_{29}$NO$_6$; C, 59.46; H, 8.51; N, 4.08. Found: C, 59.51; H, 8.50; N, 4.09.

EXAMPLE 16

Preparation of Trioxane Sulfamate Ester (27)

An oven dried 10 ml 1-necked round bottomed flask with magnetic stirring bar, serum cap, and gas-needle inlet was charged with dry THF (1 ml), n-buthyllithium (1.5M in hexane, 160 μl, 0.24 mmol) and treated with dry diisopropylamine (33 μl, 0.24 mmol) at 0° C. under argon atmosphere. This LDA solution was cooled to −78° C. and treated with trioxane alcohol 7 (33.4 mg, 0.12 mmol) in dry THF (1 ml) via cannular. After the reaction mixture was stirred for 10 min at −78° C., N,N-dimethylsulfamoyl chloride (50 μl, 0.46 mmol) was added to the reaction mixture, and then slowly warmed to room temperature over 0.5 hour. This reaction mixture was stirred for additional 7 hours and quenched with water (2 ml) at 0° C. The organic layer was extracted twice with ether (10 ml×2), combined, washed with saturated sodium chloride solution (10 ml), and dried over anhydrous magnesium sulfate, filtered, and concentrated under reduced pressure to yield a crude product which was separated by silica gel column chromatography to afford the corresponding pure trioxane sulfamate ester 27 (30.9 mg, 66%) as a colorless solid: FT-IR (CHCl$_3$) 3020, 2933, 2862, 1453, 1409, 1376, 1325, 1266, 1145, 1077, 1048, 1009, 949, 909, 871, 794; $^1$H NMR (CDCl$_3$, 400 MHz) δ 5.19 (d, J=1.2 Hz, 1H), 3.82–3.75 (m, 1H), 3.69–3.62 (m, 1H), 3.50 (s, 3H), 2.82 (s, 6H), 2.32 (ddd, J=14.7, 14.4, 3.0 Hz, 1H), 2.09–1.95 (m, 2H), 1.90–1.72 (m, 2H), 1.71–1.50 (m, 6H), 1.46–1.34 (m, 2H), 1.38 (s, 3H), 1.30–1.20 (m, 1H); $^{13}$C NMR (CDCl$_3$, 100 MHz) δ 105.26, 100.21, 85.59, 61.61, 56.66, 48.66, 41.76, 38.13, 37.52, 33.93, 31.11, 30.16, 27.11, 25.91, 25.27.

EXAMPLE 17

Preparation of Trioxane Phosphate Ester (28)

An oven dried 10 ml 1-necked round bottomed flask with magnetic stirring bar, serum cap, and gas-needle inlet was charged with diethylchlorophosphate (65 μl, 0.45 mmol) and dry methylene chloride (1 ml), and cooled to 0° C. by means of an ice bath. To this solution was added via a gas-tight syringe triethylamine (190 μl, 1.36 mmol). After the reaction mixture was slowly warmed to room temperature over 0.5 hour, and stirred for 0.5 hour and it was treated with trioxane alcohol 7 (53.3 mg, 0.20 mmol) in methylene chloride (1 ml). This solution was then refluxed for 24 hours and the solvent was removed at reduced pressure to yield a crude product which was directly separated by silica gel column chromatography to afford the corresponding pure trioxane phosphate ester 28 (41.2 mg, 52%) as a colorless oil: FT-IR (neat) 2930, 2860, 1443, 1374, 1266, 1209, 1120, 1027, 977; $^1$H NMR (CDCl$_3$, 400 MHz) δ 5.13 (d, J=1.2 Hz, 1H), 4.12 (m, 6H), 3.50 (s, 3H), 2.36–2.24 (m, 2H), 2.04–1.98 (m, 1H), 1.89–1.18 (m, 11H), 1.38 (s, 3H), 1.34 (t, J=7.0 Hz, 6H); $^{13}$C NMR (CDCl$_3$, 100 MHz) δ 105.22, 100.06, 85.08, 66.35 (d, J=5.9 Hz), 63.68 (d, J=5.8 Hz), 56.66, 48.55, 41.67, 37.45, 30.95, 30.85 (d, J=7.1 Hz), 29.34, 27.08, 25.91, 25.12, 16.14 (d, J=6.6 Hz); LRMS (NH$_3$, rel. intensity) 426 (M+18, 2), 409 (M+1, 14), 377 (4), 349 (30), 331 (5), 195 (B), 136 (8), 119 (4). HRMS (CI, NH$_3$) calcd for C$_{18}$H$_{34}$O$_8$P (M+H) 409.1991. Found 409.1995.

EXAMPLE 18

Preparation of Trioxane Carbamate Ester (31)

An oven dried 10 ml 1-necked round bottomed flask with magnetic stirring bar, serum cap, and gas-needle inlet was charged with dry THF (1 ml), n-butyllithium (1.5M in hexane, 100 μl, 0.15 mmol) and treated with dry diisopropylamine (20 μl, 0.14 mmol) at 0° C. and treated with trioxane alcohol 7 (12.3 mg, 0.05 mmol) in dry THF (1 ml) via cannular. After the reaction mixture was stirred for 5 min. at −78° C., N,N-diphenylcarbamoyl chloride (32.0 mg, 0.14 mmol) in THF (0.5 ml) was added via cannular to the reaction mixture, and then slowly warmed to room temperature over 10 min. This reaction mixture was stirred for additional 6 hours and quenched with water (5 ml) at 0° C. The organic layer was extracted twice with ether (10 ml×2), combined, washed with saturated sodium chloride solution (10 ml), and dried over anhydrous magnesium sulfate, filtered, and concentrated under reduced pressure to yield a crude product which was separated by silica gel column chromatography to afford the corresponding pure trioxane carbamate ester 31 (13.8 mg, 65%) as a colorless oil: FT-IR (CHCl$_3$) 3020, 2932, 1706, 1594, 1492, 1401, 1338, 1305, 1121, 1078, 1008, 927; $^1$H NMR (CDCl$_3$, 400 MHz) δ 7.35–7.18 (m, 10H), 5.11 (s, 1H), 4.32–4.26 (m, 1H), 4.20–4.13 (m, 1H), 3.47 (s, 3H), 2.36–2.28 (m, 1H), 2.23–2.15 (m, 1H), 2.04–1.97 (m, 1H), 1.85–1.30 (m, 10H), 1.37 (s, 3H), 1.23–1.11 (m, 1H): $^{13}$C NMR (CDCl$_3$, 100 MHz) δ 154.80, 142.60, 128:86, 127.01, 126.01, 105.16, 100.11, 85.18, 65.03, 56.68, 48.62, 42.24, 37.49, 31.03, 29.25, 29.22, 27.13, 25.95, 25.19. Anal. Calcd for C$_{27}$H$_{33}$NO$_6$: C, 69.36; H, 7.11; N, 3.00. Found: C, 69.46; H, 7.16; N, 3.11.

EXAMPLE 19

Preparation of Trioxane Sulfonate Ester (32)

An oven dried 5 ml 1-necked round bottomed flask with magnetic stirring bar, serum cap, and gas-needle inlet was charged with dansyl chloride (82.1 mg, 0.30 mmol) and dry chloroform (1 ml), and cooled to 0° C. by means of an ice bath. To this solution was added via a gas-tight syringe triethylamine (50 μl, 0.4 mmol). After the reaction mixture was slowly warmed to room temperature over 0.5 hour, and stirred for 0.5 hour and it was treated with trioxane alcohol 7 (23.7 mg, 0.09 mmol) in chloroform (1 ml). This solution was then refluxed for 4 hours and the solvent was removed at reduced pressure to yield a crude product which was directly separated by silica gel column chromatography to afford the corresponding pure trioxane sulfonate ester 32 (30.1 mg, 68%) as a greenish gum: FT-IR (neat) 3020, 2937, 2863, 1614, 1589, 1576, 1478, 1464, 1455, 1442, 1410, 1357, 1174, 1152, 1078, 1008, 948, 872; $^1$H NMR (CDCl$_3$, 400 MHz) δ 8.60 (d, J=8.4 Hz, 1H), 8.30–8.26 (m, 2H), 7.62–7.52 (m, 2H), 7.11 (d, J=7.6 Hz, 1H), 4.89 (d, J=1.2 Hz, 1H), 4.13–4.03 (m, 2H), 3.36 (s, 3H), 2.89 (s, 6H), 2.27–2.11 (m, 2H), 1.98–1.92 (m, 1H), 1.80–1.66 (M, 1h), 1.65–1.56 (M, 1h), 1.55–1.42 (m, 3H), 1.42–1.19 (m, 4H), 1.32 (s, 3H), 1.17–1.09 (m, 1H), 0.98–0.85 (m, 1H); $^{13}$C NMR (CDCl$_3$, 100 MHz) δ 151.74, 131.37, 131.36, 130.52, 129.92, 129.89, 128.64, 123.04, 119.69, 115,54, 105.18, 99.80, 84.90, 69.77, 56.56, 48.38, 45.44, 41.50, 37.35, 30.77, 29.68, 29.33, 26.98, 25.82, 24.84. Anal. Calcd for C$_{26}$H$_{35}$NO$_7$S: C, 61.76; H, 6.98; N, 2.78; S, 6.34. Found: C, 61.85; H, 7.02; N, 2.81; S, 6.34.

EXAMPLE 20

Preparation of Trioxane Phosphate Ester (33)

An oven dried 10 ml 1-necked round bottomed flask with magnetic stirring bar, serum cap, and gas-needle inlet was charged with dry THF (1 ml), n-butyllithium (1.5M in hexane, 120 μl, 0.18 mmol) and treated with dry diisopropylamine (25 μl, 0.18 mmol) at 0° C. under argon atmosphere. This LDA solution was cooled to −78° C. and treated with trioxane alcohol 7 (24.9 mg, 0.09 mmol) in dry THF (1 ml via cannular. After the reaction mixture was stirred for 5 min at −78° C., diphenyl chlorophosphate (40 μl, 0.19 mmol) was added to the reaction mixture, and then slowly warmed to room temperature over 10 min. This reaction mixture was stirred for additional two hours and quenched with water (5 ml) at 0° C. The organic layer was extracted twice with ether (10 ml×2), combined, washed with saturated sodium chloride solution (10 ml), and dried over anhydrous magnesium sulfate, filtered, and concentrated under reduced pressure to yield a crude product which was separated by silica gel column chromatography to afford the corresponding pure trioxane phosphate ester 33 (21.4 mg, 71%) as colorless oil: FT-IR (CHCl$_3$) 3020, 2932, 1593, 1490, 1284, 1162, 1024, 1010, 960; $^1$H NMR (CDCl$_3$, 400 MHz) δ 7.37–7.17 (m, 10H), 5.09 (d, J=1.2 Hz, 1H), 4.36–4.29 (m, 2H), 3.46 (s, 3H), 2.36–2.26 (m, 2H), 2.04–1.99 (m, 1H), 1.85–1.42 (m, 9H), 1.39 (s, 3H), 1.37–1.25 (m, 1H), 1.25–1.14 (m, 1H); $^{13}$C NMR (CDCl$_3$, 100 MHz) δ 150.58 (d, J=6.8 Hz), 129.75, 125.25, 120.12 (d, J=4.8 Hz), 105.26, 99.97, 85.05, 68.16 (d, J=6.5 Hz), 56.66, 48.51, 41.63, 37.44, 30.90, 30.85, 29.42, 27.06, 25.90, 25.05.

EXAMPLE 21

Preparation of Trioxane Carbamate Ester (34)

An oven dried 10 ml 1-necked round bottomed flask with magnetic stirring bar, serum cap, and gas-needle inlet was charged with dry THF (1 ml), n-butyllithium (1.5M in hexane, 240 μl, 0.36 mmol) and treated with dry dissopropylamine (50 μl, 0.36 mmol) at 0° C. under argon atmosphere. This LDA solution was cooled to −78° C. and treated with trioxane alcohol 7 (30.9 mg, 0.11 mmol) in dry THF (1 ml) via cannular. After the reaction mixture was stirred for 10 min at −78° C., N,N-diethylcarbamoyl chloride (50 μl, 0.39 mmol) was added to the reaction mixture, and then slowly warmed to room temperature over 0.2 hour. This reaction mixture was stirred for additional 4 hours and quenched with water (10 ml) at 0° C. The organic layer was extracted twice with ether (10 ml×2), combined, washed with saturated sodium chloride solution (10 ml), and dried over anhydrous magnesium sulfate, filtered, and concentrated under reduced pressure to yield a crude product which was separated by silica gel column chromatography to afford the corresponding pure trioxane carbamate ester 34 (28.9 mg, 69%) as a colorless oil: FT-IR (CHCl$_3$, cm$^{-1}$) 3020, 2934, 1679, 1432, 1378, 1278, 1206, 1178, 1077, 1009, 927.666; $^1$H NMR (CDCl$_3$, 400 MHz) δ 5.16 (d, J=1.2 Hz, 1H), 4.18 (ddd, J=10.6, 8.0, 4.8 Hz, 1H), 4.07 (ddd, J=10.6, 7.4, 7.4 Hz, 1H), 3.50 (s, 3H), 3.26 (bm, 4H), 2.37–2.21 (m, 2H), 2.05–1.99 (m, 1H), 1.89–1.48 (m, 9H), 1.44–1.15 (m, 2H), 1.38 (s, 3H), 1.12 (t, J=7.0 Hz, 6H); $^{13}$C NMR (CDCl$_3$, 100 MHz) δ 156.04, 105.18, 100.21, 85.20, 63.82, 56.70, 48.60, 42.23, 41.64, 41.20, 37.49, 31.06, 29.30, 29.15, 27.13, 25.96, 25.23, 14.01, 13.57. LRMS (NH$_3$, rel. intensity). HRMS (CI, NH$_3$).

EXAMPLE 22

Preparation of Trioxane Phosphate Ester (35)

An oven dried 10 ml 1-necked round bottomed flask with magnetic stirring bar, serum cap, and gas-needle inlet was charged with dry THF (1 ml), n-butyllithium (1.5M in hexane, 120 μl, 0.18 mmol) and treated with dry diisopropylamine (25 μl, 0.18 mmol) at 0° C. under argon atmosphere. This LDA solution was cooled to −78° C. and treated with trioxane alcohol 7 (22.8 mg, 0.08 mmol) in dry THF (1 ml) via cannular. After the reaction mixture was stirred for 10 min at −78° C., diethyl chlorothiophosphate (30 μl, 0.19 mmol) was added to the reaction mixture, and then slowly warmed to room temperature over 0.2 hour. This reaction mixture was stirred for additional 4 hours and quenched with water (10 ml) at 0° C. The organic layer was extracted twice with ether (10 ml×2), combined, washed with saturated sodium chloride solution (10 ml), and dried over anhydrous magnesium sulfate, filtered, and concentrated under reduced pressure to yield a crude product which was separated by silica gel column chromatography to afford the corresponding pure trioxane phosphate ester 35 (15.0 mg, 45%, 62% based on recovered SM (7.2 mg)) as a colorless oil: FT-IR (CHCl$_3$, cm$^{-1}$) 3020, 2994, 2933, 2862, 1443, 1376, 1266, 1135, 1121, 1024, 973, 898, 871; $^1$H NMR (CDCl$_3$, 400 MHz) δ 5.14 (d, J=1.2 Hz, 1H), 4.17-4.09 (m, 6H), 3.50 (s, 3H), 2.36-2.25 (m, 2H), 2.04-1.98 (m, 1H), 1.89-1.40 (m, 9H), 1.38 (s, 3H), 1.38-1.16 (m, 2H), 1.33 (t, J=7.0 Hz, 6H); $^{13}$C NMR (CDCl$_3$, 100 MHz) d 105.22, 100.10, 85.11, 66.93 (d, J=5.4 Hz), 64.25 (d, J=4.7 Hz), 56.69, 48.56, 41.71, 37.46, 30.97, 30.68 (d, J=7.1 Hz), 29.38, 27.10, 25.92, 25.12, 15.93 (d, J=7.5 Hz). LRMS (NH$_3$, rel. intensity). HRMS (CI, NH$_3$).

EXAMPLE 23

Preparation of Trioxane Ether (101)

An oven dried 5 ml 1-necked round bottomed flask with magnetic stirring bar, serum cap, and gas-needle inlet was charged with trioxane alcohol 7 (34.2 mg, 0.13 mmol) and dry N,N-dimethylformamide (0.5 ml), and methyl iodide (100 μl, 1.6 mmol) via a gas-tight syringe, and cooled to 0° C. under argon atmosphere. To this solution was treated sodium hydride (60% dispersion on mineral oil, ca 20 mg, 0.5 mmol). After being stirred for 10 min at 0° C., the reaction mixture was slowly warmed to room temperature, stirred for 15 hours. The reaction mixture was then cooled to 0° C., and quenched with water (1 ml). The organic layer was extracted twice with ether (5 ml×2), washed with saturated NaCl solution (5 ml), dried over anhydrous MgSO$_4$, filtered and concentrated under reduced pressure. The residue was directly purified by silica gel column chromatography to afford the corresponding trioxane ether 101 (17.4 mg, 48%, 66% based on recovered starting material) as a colorless oil: FT-IR (CHCl$_3$); $^1$H NMR (CDCl$_3$, 400 MHz) δ 5.15 (d, J=1.6 Hz, 1H), 3.49 (s, 3H), 3.47-3.42 (m, 2H), 3.33 (s, 3H), 2.36-2.19 (m, 2H), 2.04-1.98 (m, 1H), 1.88-1.44 (m, 9H), 1.38 (s, 3H), 1.36-1.19 (m, 2H); $^{13}$C NMR (cDCl$_3$, 100 MHz) δ 105.16, 100.32, 85.38, 71.57, 58.32, 56.67, 48.59, 42.14, 37.53, 31.11, 29.75, 29.56, 27.19, 25.96, 25.27.

EXAMPLE 24

Preparation of Trioxane Ether (102)

An oven dried 5 ml 1-necked round bottomed flask with magnetic stirring bar, serum cap, and gas-needle inlet was charged with trioxane alcohol 7 (12.1 mg, 0.04 mmol) and dry N,N-dimethylformamide (0.5 ml), and benzylbromide (25 μl, 0.2 mmol) via a gas-tight syringe, and cooled to 0° C. under argon atmosphere. To this solution was treated sodium hydride (60% dispersion on mineral oil, ca 10 mg, 0.25 mmol). After being stirred for 10 min at 0° C., the reaction mixture was slowly warmed to room temperature, stirred for 17 hours. Then the reaction mixture was warmed to 60° C., and stirred for 1 hour. The reaction mixture was then cooled to 0° C., and directly separated by silica gel column chromatography to afford the corresponding trioxane ether 102 (5.1 mg, 32%, 67% based on recovered starting material) as a colorless oil: FT-IR (CHCl$_3$) 3020, 2932, 2862, 1602, 1454, 1376, 1265, 1135, 1121, 1092, 1007, 962, 927, 897, 871, 700; $^1$H NMR (CDCl$_3$, 400 MHz) δ 7.34 (d, J=4.8 Hz, 4H), 7.28 (m, 1H), 5.15 (s, 1H), 4.53 (d, J=12.0 Hz, 1H), 4.49 (d, J=12.0 Hz, 1H), 3.54 (m, 2H), 3.49 (s, 3H), 2.32 (m, 1H), 2.28 (m, 1H), 2.01 (m, 1H), 1.89-1.48 (m, 8H), 1.38 (s, 3H), 1.41-1.17 (m, 1H); $^{13}$C NMR (CDCl$_3$, 100 MHz) δ 138.57, 128.33, 127.68, 127.46, 105.15, 100.33, 85.36, 72.66, 69.22, 56.73, 48.55, 42.16, 37.50, 31.08, 29.86, 29.49, 27.16, 25.95, 25.23.

EXAMPLE 25

Preparation of Trioxane Ether (103)

An oven dried 5 ml 1-necked round bottomed flask with magnetic stirring bar, serum cap, and gas-needle inlet was charged with trioxane alcohol 7 (27.5 mg, 0.1 mmol) and dry N,N-dimethylformamide (0.5 ml), and diethyl chloromethylphosphonate (40 μl, 0.26 mmol) via a gas-tight syringe, and cooled to 0° C. under argon atmosphere. To this solution was treated sodium hydride (60% dispersion on mineral oil, ca 10 mg, 0.25 mmol). After being stirred for 10 min at 0° C., the reaction mixture was slowly warmed to room temperature, stirred for 2 hours. The reaction mixture was then cooled to 0° C., and quenched with water (1 ml). The organic layer was extracted twice with ether (5 ml×2), washed with saturated NaCl solution (5 ml), dried over anhydrous MgSO$_4$, filtered and concentrated under reduced pressure. The residue was directly purified by silica gel column chromatography to afford the corresponding trioxane ether 103 (25.3 mg, 60%, 65% based on recovered starting material) as a colorless oil: FT-IR (CHCl$_3$) 3019, 2933, 2862, 1443, 1398, 1376, 1265, 1135, 1121, 1012, 963, 897, 872, 838; $^1$H NMR (cDCl$_3$, 400 MHz) δ 5.13 (s, 1H), 4.21-4.07 (m, 6H), 3.57 (d, J=10.4 Hz, 1H), 3.56 (d, J=10.4 Hz, 1H), 3.50 (s, 3H), 2.36-2.26 (m, 2H), 2.01 (m, 1H), 1.89-1.43 (m, 10H), 1.38 (t, J=7.2 HZ, 6H), 1.38 (s, 3H), 1.29-1.19 (m, 1H); $^{13}$C NMR (CDCl$_3$, 100 MHz) δ 105.27, 100.03, 85.10, 66.04, 65.99, 63.51, 56.69, 48.55, 41.54, 37.44, 33.41 (d, J=159.6 Hz), 31.17, 30.94, 29.37, 27.07, 25.91, 25.11, 16.44.

EXAMPLE 26

Preparation of Trioxane Ether (104)

An oven dried 5 ml 1-necked round bottomed flask with magnetic stirring bar, serum cap, and gas-needle inlet was charged with trioxane alcohol 7 (14.0 mg, 0.05 mmol) and dry N,N-dimethylformamide (0.5 ml), and allyl bromide (50 μl, 0.58 mmol) via a gas-tight syringe, and cooled to 0° C. under argon atmosphere. To this solution was treated sodium hydride (60% dispersion on mineral oil, ca 10 mg, 0.25 mmol). After being stirred for 10 min at 0° C., the reaction mixture was slowly warmed to room temperature, stirred for 4 hours. The reaction mixture was then cooled to 0° C., and quenched with water (1 ml). The organic layer was extracted twice with ether (5 ml×2), washed with saturated NaCl solution (5 ml), dried over anhydrous MgSO$_4$, filtered and concentrated under reduced pressure. The residue was directly purified by silica gel column chromatography to afford the corresponding trioxane ether 104 (9.1 mg, 57%, 68% based on recovered starting material) as a colorless oil: FT-IR (CHCl$_3$) 3018, 2932, 2861, 1644, 1443, 1376, 1266, 1121, 1092, 1005, 928, 896, 871, 795; $^1$H NMR (CDCl$_3$, 400 MHz) δ 5.92 (ddt, J=17.2, 10.4, 5.6 Hz, 1H), 5.27 (ddd, J=17.2, 1.8, 1.2 Hz, 1H), 5.15 (d, J=1.2 Hz, 1H), 3.97 (m, 2H), 3.49 (s, 3H), 3.52-3.47 (m, 2H), 2.32 (ddd, J=14.2, 14.2, 3.5 Hz, 1H), 2.28-2.20 (m, 1H), 2.01 (ddd, J=14.2, 4.5, 3.0 Hz, 1H), 1.89-1.48 (m, 8H), 1.38 (s, 3H), 1.37-1.19 (m, 3H); $^{13}$C NMR (CDCl$_3$, 100 MHz) δ 135.00, 116.76, 105 15, 100.33, 85.36, 71.61, 69.30, 56.74, 48.54, 42.24, 37.49, 31.08, 29.91, 27.15, 25.96, 25.24.

EXAMPLE 27

Preparation of Trioxane Ether (105)

An oven dried 5 ml 1-necked round bottomed flask with magnetic stirring bar, serum cap, and gas-needle inlet was charged with trioxane alcohol 7 (36.8 mg, 0.14 mmol) and dry N,N-dimethylformamide (0.5 ml), and 4-(chloromethyl)-3,5-dimethylisoxazole (40 μl, 0.32 mmol) via a gas-tight syringe, and cooled to 0° C. under argon atmosphere. To this solution was treated sodium hydride (60% dispersion on mineral oil, ca 10 mg, 0.25 mmol). After being stirred for 10 min at O° C., the reaction mixture was slowly warmed to room temperature, stirred for 2 hours. The reaction mixture was then cooled to 0° C., and quenched with water (1 ml). The organic layer was extracted twice with ether (5 ml×2), washed with saturated NaCl solution (5 ml), dried over anhydrous MgSO$_4$, filtered and concentrated under reduced pressure. The residue was directly purified by silicia gel column chromatography to afford the corresponding trioxane ether 105 (31.7 mg, 61%, 65% based on recovered starting material) as a colorless oil: FT-IR (CHCl$_3$) 3009, 2933, 2862, 1638, 1453, 1409, 1376, 1266, 1136, 1121, 1079, 1007, 963, 925, 896, 871, 838, 797; $^1$H NMR (CDCl$_3$, 400 MHz) δ 5.13 (s, 1H), 4.29 (d, J=12.0 Hz, 1H), 4.22 (d, J=12.0 Hz, 1H), 3.50–3.44 (m, 2H), 3.48 (s, 3H), 2.38 (s, 3H), 2.38–2.27 (m, 1H), 2.27 (s, 3H), 2.27–2.19 (m, 1H), 2.01 (ddd, J=14.2, 5.0, 3.2 Hz, 1H), 1.89–1.47 (m, 8H), 1.38 (s, 3H), 1.38–1.16 (m, 2H); $^{13}$C NMR (CDCl$_3$, 100 MHz) δ 167.07, 159.92, 111.24, 105.18, 100.20, 85.30, 66.04, 68.71, 61.16, 56.68, 48.59, 41.93, 37.47, 31.02, 29.73, 29.49, 27.10, 25.93, 25.21, 11.02, 10.09.

EXAMPLE 28

Preparation of Trioxane Ether (106) and its Sodium Salt (107))

An oven dried 5 ml 1-necked round bottomed flask with magnetic stirring bar, serum cap, and gas-needle inlet was charged with trioxane alcohol tosylate 23 (20.0 mg, 0.05 mmol) and dry tetrahydrofuran (1 ml), and methylglycolate (60 μl, 0.78 mmol) via a gas-tight syringe, and cooled to 0° C. under argon atmosphere. To this solution was treated sodium hydride (60% dispersion on mineral oil, ca 10 mg, 0.25 mmol) and dry dimethylsulfoxide (1 ml). After being stirred for 10 min at 0° C., the reaction mixture as slowly heated to 65° C., refluxed for 12 hours. The reaction mixture was then cooled to 0° C., quenched with water (1 ml), and acidified with saturated sodium bisulfate (2 ml). The organic layer was extracted twice with ether (5 ml×2), washed with saturated NaCl solution (5 ml), dried over anhydrous MgSO$_4$, filtered and concentrated under reduced pressure. The residue was directly purified by silica gel column chromatography to afford the corresponding trioxane ether 106 (7.2 mg, 46%) as white solid. This pure trioxane ether 106 (0.4 mg, 1.2 μmol) in a 500 μl vial was dissolved in methanol (100 μl) and treated with 5% sodium bicarbonate solution (2 mg, 1.2 μmol) and then concentrated to give the corresponding sodium salt 107. Trioxane ether 106: FT-IR (CHCl$_3$) 3683, 3548, 3020, 2933, 1736, 1443, 1376, 1121, 1086, 1009, 928; $^1$H NMR (CDCl$_3$, 400 MHz) δ 5.15 (d, J=1.2 Hz, 1H), 4.35–4.22 (m, 2H), 4.16 (d, J=5.2 Hz, 2H), 3.50 (s, 3H), 2.37–2.21 (m, 2H), 2.05–1.99 (m, 1H), 1.88–1.75 (m, 1H), 1.74–1.50 (m, 3H), 1.49–1.39 (m, 6H), 1.38 (s, 3H), 1.36–1.19 (m, 2H); $^{13}$C NMR (CDCl$_3$, 100 MHz) δ 105.32, 100.16, 85.14, 64.52, 60.63, 56.65, 48.58, 42.08, 37.47, 30.96, 29.50, 29.25, 27.07, 25.90, 25.15.

EXAMPLE 29

Preparation of Trioxane Iodide (301)

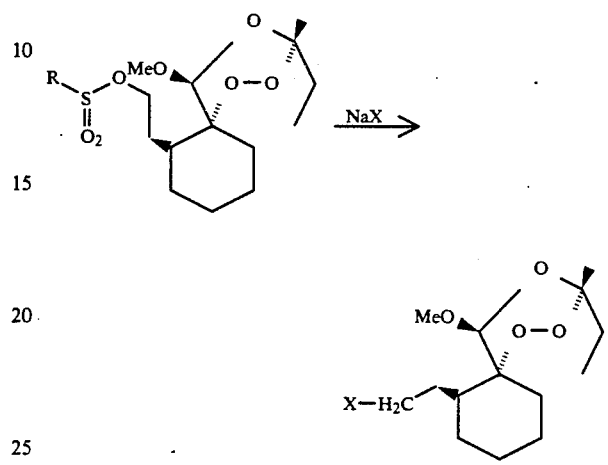

An oven dried 5 ml 1-necked round bottomed flask with magnetic stirring bar, serum cap, and gas-needle inlet was charged with trioxane alcohol tosylate 23 (31.5 mg, 0.07 mmol) and dry acetone (3 ml), and sodium iodide (240 mg, 1.6 mmol). Then the reaction mixture was refluxed for 2 hours. The reaction mixture was then cooled to 0° C., and diluted with water (5 ml). The organic layer was extracted twice with ether (10 ml×2), washed with saturated NaCl solution (5 ml), dried over anhydrous MgSO$_4$, filtered and concentrated under reduced pressure. The residue was directly purified by silica gel column chromatography to afford the corresponding trioxane iodide 301 (25.8 mg, 91%) as a colorless oil: FT-IR (CHCl$_3$) 3020, 2932, 2861, 1442, 1408, 1376, 1267, 1170, 1140, 1122, 1009, 959, 895, 871, 726, 724, 672, 666; $^1$H NMR (CDCl$_3$, 400 MHz) δ 5.09 (s, 1H), 3.50 (s, 3H), 3.33 (ddd, J=9.6, 9.6, 4.4 Hz, 1H), 3.16 (ddd, J=9.6, 9.6, 7.6 Hz, 1H), 2.44 (m, 1H), 2.33 (ddd, J=13.3, 13.3, 3.0, 1H), 2.01 (m, 1H), 1.89–1.46 (m, 9H), 1.38 (s, 3H), 1.34–1.20 (m, 2H); $^{13}$C NMR (CDCl$_3$, 100 MHz) δ 105.29, 100.10, 85.19, 56.68, 48.54, 46.32, 37.41, 34.88, 30.91, 28.79, 27.04, 25.89, 25.06, 5.06.

EXAMPLE 30

This example illustrates the preparation of trioxanes (10) and (13):

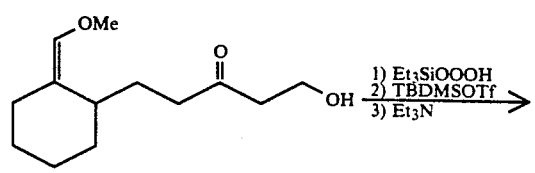

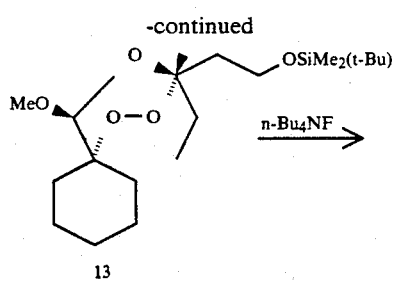

13

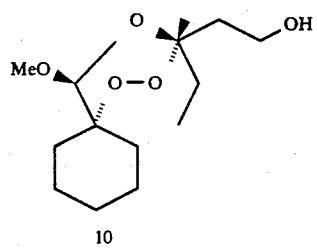

10

Preparation of Trioxane (13)

To the Et₃SiOOOH solution (24 ml, 1.0 mmol) was cannulated the reactant hydroxy enol ether (21.9 mg, 0.10 mmol) in CH$_2$Cl$_2$ (2 ml) solution over 10 seconds at −78° C. under nitrogen atmosphere. To the resultant solution, after being vigorously stirred for 30 min, was slowly added pre-cooled TBDMSOTf (45 μl, 0.20 mmol) in dichloromethane (1.0 ml) over 1 min. The resultant solution was stirred at −78° C. for 5 hours, treated with saturated sodium bicarbonate solution (10 ml), and then slowly warmed to 0° C. over one hour. The organic layer was separated from the aqueous layer, dried over anhydrous magnesium sulfate, filtrated, and concentrated to 1 ml under reduced pressure. The separation of the crude product with ethyl acetate and hexane (1:99) gave a pure, 1,2,4-trioxane 13 (>95% pure, 8.4 mg, 23%): $^1$H NMR (CDCl$_3$, 400 MHz) δ 4.895 (s, 1H), 3.84–3.71 (m, 2H), 3.511 (s, 3H), 2.26–2.13 (m, 1H), 2.05–2.00 (m, 1H), 1.948 (t, J=7.2 Hz, 2H), 1.86–1.50 (m, 7H), 1.44–1.15 (m, 4H), 0.885 (s, 9H), 0.052 (s, 6H); HRMS (Chemical Ionization) calcd for C$_{19}$H$_{37}$O$_5$Si 373.2410. Found 373.2414.

Preparation of Trioxane (10)

To the protected trioxane 13 (10.2 mg, 0.03 mmol) in dry ether (3 ml) was added 1M THF solution of tetrabutylammonium fluoride (50 μl, 0.05 mmol) at room temperature. The resulting solution was stirred for 6 hours, and then concentrated to give a crude product, which was directly separated by column chromatography to afford the corresponding deprotected trioxane 10 (5.2 mg, 74%) as a colorless oil: $^1$H NMR (CDCl$_3$, 400 MHz) δ 4.977 (s, 1H), 3.812 (q, J=6.11 Hz, 2H) 3.523 (s, 3H), 2.34–2.25 (m, 1H), 2.12–1.54 (m, 13H), 1.29–1.18 (m, 2H).

Representative compounds according to the invention were subjected to in vitro screening using a modification of the semiautomated microdilution techniques of Desjardins, et al., *Antimicrob. Agents Chemother,* 1979, 16, 710 and Milhous et al., *Antimicrob. Agents Chemother,* 1985, 27, 525. Two *P. falciparum* malaria parasite clones, designated as Indochina (W-2) and Sierra Leone (D-6), were utilized in susceptibility testing. Test compounds were dissolved in DMSO and serially diluted with culture media. The uptake of tritiated hypoxanthine was used as an index of inhibition of parasite growth.

In carrying out the tests, the test compounds were dissolved in DMSO and diluted in culture medium with plasma to allow for a starting concentration of 1000×10$^{-9}$M and five-fold dilutions performed down to 0.06×10$^{-9}$M. This allowed for a well-defined concentration response for control drugs.

The activity results shown in Table III were obtained:

TABLE III

| Compound | INDOCHINA CLONE | | AFRICAN (D-6, SIERRA LEONE CLONE) | |
|---|---|---|---|---|
| | IC$_{60}$ | IC$_{90}$ | IC$_{60}$ | IC$_{90}$ |
| −19 | <0.54 | | <0.54 | |
| −20 | 1.61 | 24.7 | 6.20 | 20.37 |
| −21 | <0.67 | | <0.67 | |
| −22 | ~70 | | 55.93 | 857.1 |
| −23 | 0.79 | 10.25 | 2.38 | 19.0 |
| −24 | 6.19 | 19.7 | 5.13 | 58.8 |
| −25 | <1.05 | | 1.5 | 4.43 |
| −26 | 0.28 | 1.29 | 0.99 | 3.93 |
| −27 | 5.31 | 23.0 | 10.38 | 30.25 |
| −28 | <0.36 | | 0.45 | 0.99 |
| −101 | 1.06 | 4.62 | 3.05 | 13.7 |
| −36 | 10.89 | 46.09 | 21.79 | 115.4 |
| Controls | | | | |
| Mefloquine | 0.02 | | 6.6 | |
| Chloroquine | 26.6 | | 1.32 | |
| Artemisinin | 00.4 | | 1.10 | |
| Arteether | ~0.03 | | 0.44 | |
| Quinine | ND | | 2.22 | |

Further test results are shown in Table IV:

TABLE IV

| Compound No. | Start Concen | W2 IC50 | W2 IC90 | D6 IC50 | D6 IC90 |
|---|---|---|---|---|---|
| 16 | 2500 | 6.84 | 57.84 | 31.67 | 78.71 |
| 31 | 2500 | <0.16 | <0.18 | 0.27 | 2.25 |
| 32 | 2500 | 1.04 | 7.17 | 5.16 | 10.01 |
| 33 | 2500 | <0.16 | <0.16 | 0.52 | 5.01 |
| 34 | 4062 | <0.28 | <0.28 | 0.39 | 1.18 |
| 35 | 2500 | 0.29 | 1.39 | 0.97 | 5.16 |
| 36 | 2500 | 24.19 | 979.18 | 255.62 | 516.21 |
| 37 | 2500 | 25.83 | 75.24 | 28.91 | 1326.71 |
| 102 | 2500 | 0.25 | 1.53 | 1.22 | 3.27 |
| 103 | 5000 | 0.96 | 8.2 | 3.03 | 29.86 |
| 104 | 2500 | 0.32 | 2.37 | 1.08 | 15.65 |
| 105 | 5000 | 0.34 | 1.64 | 1.82 | 19.09 |
| 106 | 2500 | 5.09 | 56.04 | 65.45 | 188.82 |
| 107 | 2500 | 1.67 | 44.48 | ~25 | ~25 |
| 301 | 5000 | <0.32 | <0.32 | 1.14 | 6.33 |

| | Controls | |
|---|---|---|
| Drug | W2 IC50 | D6 IC50 |
| CQ | 61.67 | 1.21 |
| MFQ | 0.11 | 3.53 |
| PYR | >250 | 1.08 |
| ART | 0.68 | 0.69 |

< LESS THAN
> GREATER THAN
~ APPROXIMATELY
CQ = CHLOROQUINE
MFQ = MEFLOQUINE
PYR = PYRIMETHAMINE
ART = ARTEMISININ

The results given in Tables III and IV show that the compounds of the invention demonstrate significant anti-malarial activity with some of the compounds showing substantially greater activity than the control compounds as indicated by the lower IC$_{50}$ and IC$_{90}$ values. These represent the concentration of test compound required to obtain 50% and 90% inhibition, respectively. Particularly significant activities are shown by, for example, compounds (19), (21), (25), (28), (31) and (33) which demonstrate substantial improvement over artemisinin.

To provide a basis for calibrating the effectiveness of the present results, the concentrations ($10^{-9}$ molar) required for 50% inhibition ($IC_{50}$) for various known anti-malarial drugs as published in the literature are set out in Table V:

TABLE V

Fifty Percent Inhibitory Concentrations ($10^{-9}$ Molar)

| Antimalarial Drug | W-2 Indochine Clone Artemisinin Indices* | D-6 Sierra Leone Clone Artemisinin Indices* | | |
|---|---|---|---|---|
| Arteether (alpha) | 03.07 | (2.08) | 04.18 | (2.52) |
| Arteether (beta) | 02.97 | (2.18) | 04.07 | (2.58) |
| Artemether | 03.34 | (1.92) | 04.49 | (2.34) |
| Artemisinin | 06.41 | (1.00) | 10.53 | (1.00 |
| Artelinic Acid | 03.30 | (1.94) | 09.73 | (1.08) |
| Dihydroartemisinin | 01.79 | (3.58) | 01.83 | (5.75) |
| Chloroquine | 99.97 | (0.06) | 10.84 | (0.97) |
| Mefloquine | 05.75 | (1.11) | 33.38 | (0.31) |
| Pyrimethamine | 176.20 | (0.03) | 00.04 | (26.11) |
| Halofantrine | 00.76 | (8.43) | 07.80 | (1.35) |
| Sulfadoxine | 80645.76 | (<0.01) | 89.39 | (0.11) |
| Quinine | 139.80 | (0.04) | 42.71 | (0.09) |

*Artemisinin indices represent intrinsic equimolar activity of each drug relative to the simultaneous artemisinin control. Source: Div Exper Theraps/WRAIR/June 87/Milhous Review of the data given in Tables I-IV shows that the present compounds are, generally speaking, substantively more active than the known anti-malarials used as controls. As noted earlier, particularly preferred compounds according to the invention are the carboxylate esters (19) and (21), carbamates (31) and (34) and phosphates (28) and (33) which are comparable in potency to arteether and have higher potency than artemisinin.

The compounds of the invention may be prepared using singlet molecular oxygen or by the method we have described in the Tetrahedron Letters, Vol. 32, No. 34, pages 4235-4238 (1991), the contents of which are incorporated herein by reference. According to that method, triethylsilyl hydrotrioxide ($Et_3SiOOOH$) is used for dioxetane formation to prepare the antimalarial 1,2,4-trioxanes.

As noted earlier, Jefford has shown that $^1O_2$ can be used to prepare 1,2,4-trioxane(c) as shown directly below from keto vinyl ether (a) in 48% yield as a structurally simplified and yet still potent version of naturally-occurring anti-malarial artemisinin (Tetrahedron Letters, 1989, 30, 4485). Using Jefford's starting keto vinyl ether (a), $Et_3SiOOOH$ has been used to generate intermediate dioxetane (b) as indicated by 400 MHz $^1H$ NMR spectroscopy (singlet at δ 5.35) as well as by weak chemiluminescence upon heating a very small amount of (b) on a tlc plate. Treating dioxetane (b) with t-butyldimethylsilyl trifluoromethanesulfonate (TBDMSOTf) produced 1,2,4-trioxane (c) isolated as a single diastereomer in 58% yield (eq. 3).

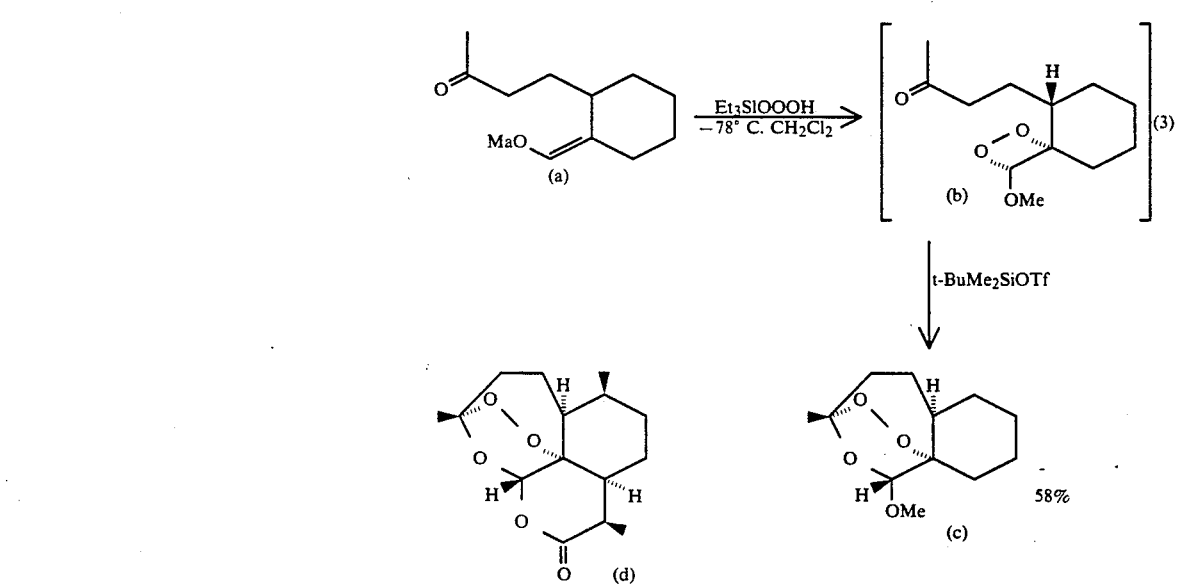

A typical experimental procedure for preparation of trioxane (c) is as follows: To the freshly-prepared (<1 minute old) $CH_2Cl_2$ solution of $Et_3SiOOOH$ (80 mL, 3.2 mmol)[1] at $-78°$ C. was cannulated methoxy vinyl ether (a) (63 mg, 0.32 mmol) in $CH_2Cl_2$ (3 ml) solution over 10 second sat under nitrogen atmosphere. To the resultant solution, after being vigorously stirred for 30 min., was slowly added pre-cooled ($-78°$ C.) TDMSOTf (80 μL 0.35 mmol) in $CH_2Cl_2$ (1.0 mL) over 1 min. The resultant solution was stirred at $-78°$ C. for 15 hours, treated with triethylamine (680 μL, 4.9 mmol), and then slowly warmed to $-20°$ C. over one hour and then to room temperature. Column chromatographic purification with ethyl acetate and hexane (2.98) gave 1,2,4-trioxane (c) (42 mg, 58%) as a white solid having the same spectral characteristics as recrystallized material. Recrystallization from hexane afforded white crystals: mp 68°-69° C., FT-IR ($CHCl_3$) 3019.7, 2951.5, 2934.1, 2862.1, 1446.0, 1396.8, 1375.5, 1270.4, 1224.2, 1212.4, 1205.8, 1142.6, 1119.9, 1066.3, 1028.8, 1009.0, 972.2, 895.8, 876.7, 865.0, 815.8 $cm^{-1}$; $^1H$ NMR ($CDCl_3$, 400 MHz) δ 4.93 (s, 1H), 3.52 (s, 3H), 2.30 (ddd, J=14.7, 13.4, 3.8Hz, 1H). 2.05 (ddd, J=14.7, 4.4, 3.1 Hz, 1H), 1.86-1.84 (m, 1H), 1.84-1.80 (m, 1H 1.70-1.50 (m, 7H), 1.40 (s, 3H) 1.28-1.16 (m, 1h); $^{13}c$ nmr ($CDCl_3$, 100 MHz) δ 104.93, 104.68, 83.40, 57.08, 47.44, 37.86, 35.69, 30.86, 26.81, 26.22, 25.05, 23.78; CIMS ($NH_3$), m/3 relative intensity 246 (M+18, 100), 229 (M+H+, 42), 214 (39), 211 (91), 197 (63), 196 (59), 186 (20), 179 (60), 169 (92), 151 (36), 138 (89), 125 (33). Anal. Calcd. for $C_{13}H_{20}O_4$; C, 63.10; H, 8.83. Found; C, 63.10, H 8.83.

Formation of dioxetanes using fresh $Et_3SiOOOH$ and subsequent structural rearrangements into 1,2,4-trioxanes were applied also to other easily prepared keto vinyl ethers like (a). For example, the gem-dimethylcyclohexyl system (e), prepared from 4,4-dimethylcyclohexanone following Jefford's procedure, produced trioxane (f) in 42% yield (eq. 4), and benzyl vinyl ether (g) gave trioxane (h) in 48% yield (eq. 5).

The benzyl vinyl ether (g) was prepared by acid catalyzed ether exchange between enzyl alcohol and 3-(2'-methoxy-vinylcyclohexyl) proprionitrile; cf, Buchi, G; White, J. D., *J. Am. Chem. Soc.*, 1964, 86, 2884.

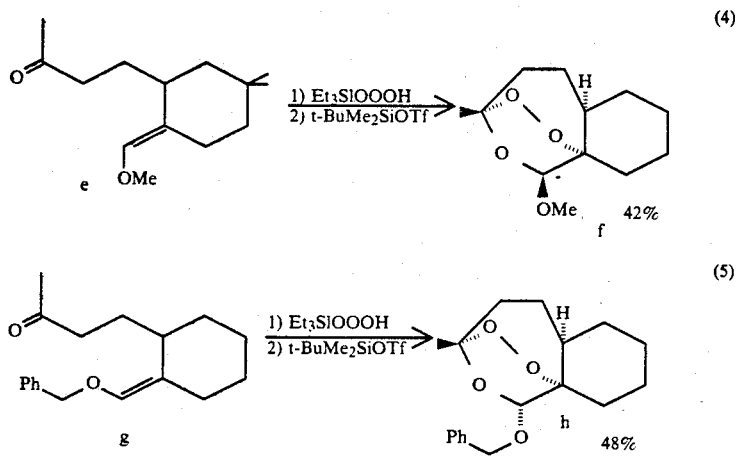

(4)

(5)

Biological in vitro evaluation of these trioxanes for anti-malarial activity against *P falciparum* clones revealed the results indicated in Table VI.

TABLE VI

| | Anti-malarial in vitro Testing Against *P. Falciparum* Clones | | |
|---|---|---|---|
| Compound | $IC_{60}$ (D-6 African Clone) | $IC_{60}$ (W-2 Indochina Clone) | Ratio of D-6/W-2 |
| c | 12.10 | 30.40 | 0.4 |
| f | 50.50 | 1.74 | 29 |
| h | 13.93 | 0.86 | 16 |
| Artemisinin | 1.56 | 0.65 | 2.4 |
| Quinine | 20.05 | 51.69 | 0.4 |
| Chloroquine | 3.53 | 30.40 | 0.1 |

Several aspects of the results in Table VI are noteworthy. First, synthetic trioxanes (f) and especially (h) are similar to natural and clinically useful antemisinin in anti-malarial activity in the W-2 Indochina clone. Second, synthetic trioxane (h) has 60 times higher anti-malarial activity than quinine in the W-2 Indochina clone. Third, both synthetic trioxanes (f) and (h) showed a pattern of anti-malarial activity completely different from that of quinine and chloroquine, with higher activity in the W-2 clone versus the D-6 clone.

The invention contemplates the use of the present compounds in conventional types of formulations as generally used in the treatment of malaria. These compositions and the methods of use are similar to those used with anteminisin. Thus, compositions containing the present 1,2,4-trioxane derivatives as the active anti-malarial component may be in the form of oral or injectable formulations or the like intended for conventional administration with the usual carriers and, if desired, auxiliary or additional components. Dosages will necessarily vary depending on the circumstances, e.g. the activity of the compound involved, but can be readily determined based on the activity of the compound compared to, for example, artemisinin. Normally dosages will be in the range of 0.1 to 100 milligrams daily per kilogram body weight.

It will be appreciated that various modifications may be made in the invention as described herein. Hence, the scope of the invention is defined in the following claims herein.

We claim:

1. An anti-malarial 1,2,4-trioxane of the formula:

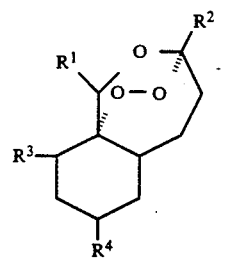

(I)

and the enantiomers thereof, wherein:

$R^1$ is lower alkoxy, aryloxy or aralkoxy;

$R^2$ is lower alkyl, hydroxy substituted-lower alkyl or ester or ether derivatives of such hydroxy substituted-lower alkyl;

$R^3$ is $-(CH_2)_mQ$ where Q is halogen or $-OR^5$ where $R^5$ is hydrogen, lower alkyl, lower alkenyl, lower alkynyl, cycloalkyl, aryl, aralkyl or heteroaralkyl, or
$R^5$ is

where
Y is C, S or P,
Z is O or S,
R is hydrogen, lower alkyl, lower alkenyl, lower alkynyl, cycloalkyl, lower alkoxy, aryloxy, aryl, aralkyl, mono- or di-lower alkylamino or mono- or di-arylamino;
n is 1 or 2;
y is 1 or 2; and
m is 1, 2, 3 or 4; and
$R^4$ is hydrogen or one or two lower alkyl.

2. A compound according to claim 1 wherein $R^1$ is methoxy, $R^2$ is methyl, $R^4$ is hydrogen and $R^5$ is —$(CH_2)_mQ$ where m is 2 and Q is $OR^5$ and $R^5$ is

where R is hydrogen, lower alkyl, aryl, mono- or di-lower alkylamino or mono- or di-arylamino.

3. A compound according to claim 1 wherein $R^1$ is methoxy, $R_2$ is methyl, $R^4$ is hydrogen and $R^5$ is —$(CH_2)_mQ$ wherein m is 2 and Q is —$OR^5$ wherein $R^5$ is either

or

where R is alkyl, aryl, alkoxy or aryloxy.

4. A compound according to claim 2 wherein R is phenyl carrying a —COOMe substituent.

5. A compound according to claim 2 wherein R is phenyl carrying a

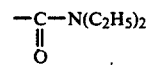

substituent.

6. A 1,2,4-trioxane according to claim 1 or 3 of the following formula:

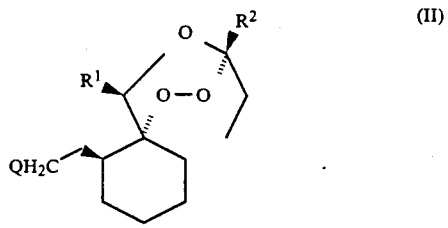

where $R^1$, $R^2$ and Q have the meanings given in claim 1.

7. A compound according to claim 6 wherein $R^1$ is methoxy and $R^2$ is methyl.

8. A pharmaceutical composition comprising a compound according to claim 1 and a pharmaceutically acceptable carrier therefor.

9. A method for treating malaria which comprises administering doses to those in need of such treatment, an effective amount of a compound according to claim 1.

* * * * *

UNITED STATES PATENT AND TRADEMARK OFFICE
CERTIFICATE OF CORRECTION

PATENT NO. : 5,225,437
DATED : July 6, 1993
INVENTOR(S) : POSNER et al.

It is certified that error appears in the above-indentified patent and that said Letters Patent is hereby corrected as shown below:

The wedge-shaped bond is missing from the following ring structures:

Column 3, line 45, should be

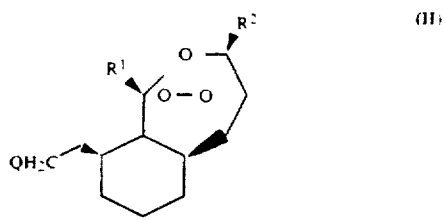

Column 3, line 63, should be

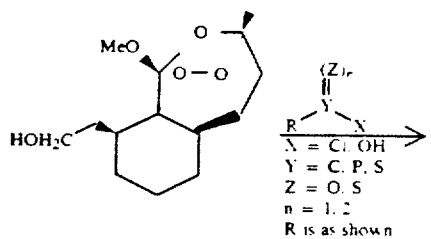

Column 4, line 5, should be

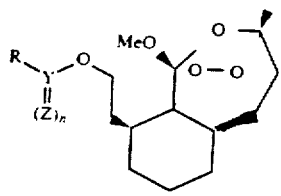

UNITED STATES PATENT AND TRADEMARK OFFICE
CERTIFICATE OF CORRECTION

PATENT NO. : 5,225,437
DATED : July 6, 1993
INVENTOR(S) : POSNER et al.

It is certified that error appears in the above-indentified patent and that said Letters Patent is hereby corrected as shown below:

Column 5, line 25, both structures, should be

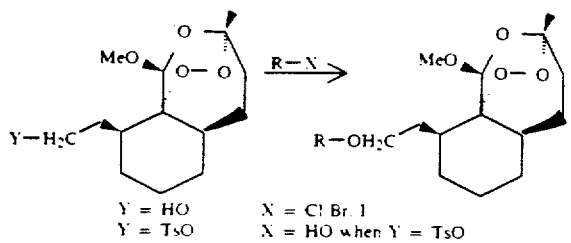

Column 6, line 5, both structures, should be

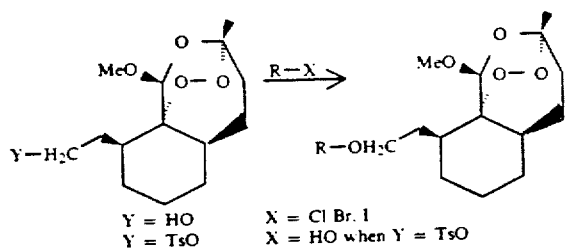

UNITED STATES PATENT AND TRADEMARK OFFICE
CERTIFICATE OF CORRECTION

PATENT NO. : 5,225,437
DATED : July 6, 1993
INVENTOR(S) : POSNER et al.

It is certified that error appears in the above-indentified patent and that said Letters Patent is hereby corrected as shown below:

Column 7, line 10, should be

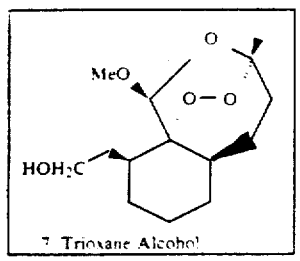

Column 7, line 20, should be

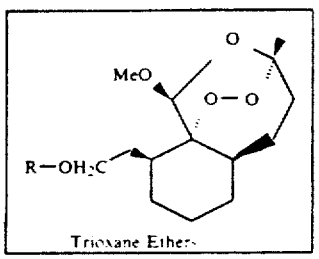

UNITED STATES PATENT AND TRADEMARK OFFICE
CERTIFICATE OF CORRECTION

PATENT NO. : 5,225,437
DATED : July 6, 1993
INVENTOR(S) : POSNER et al.

It is certified that error appears in the above-indentified patent and that said Letters Patent is hereby corrected as shown below:

Column 7, line 40, should be

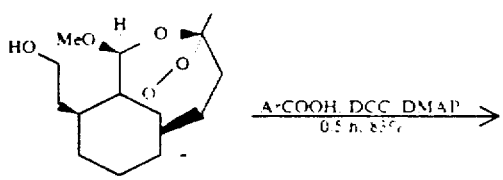

Column 7, line 45, should be

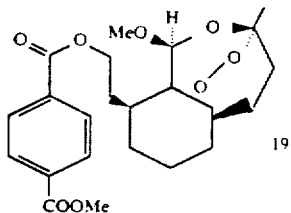

UNITED STATES PATENT AND TRADEMARK OFFICE
CERTIFICATE OF CORRECTION

PATENT NO.   :   5,225,437
DATED        :   July 6, 1993
INVENTOR(S)  :   POSNER et al.

It is certified that error appears in the above-indentified patent and that said Letters Patent is hereby corrected as shown below:

Column 7, line 63, should be

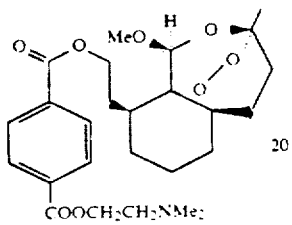

Column 8, line 10, should be

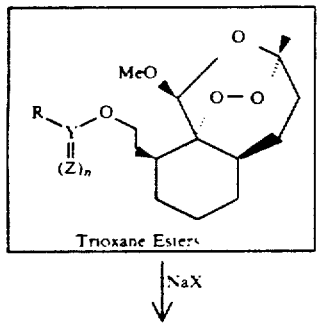

UNITED STATES PATENT AND TRADEMARK OFFICE
CERTIFICATE OF CORRECTION

PATENT NO. : 5,225,437
DATED : July 6, 1993
INVENTOR(S) : POSNER et al.

It is certified that error appears in the above-indentified patent and that said Letters Patent is hereby corrected as shown below:

Column 8, line 20, should be

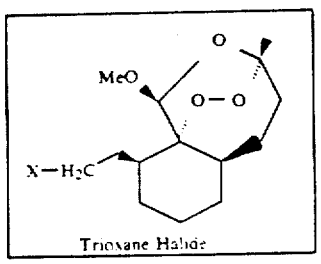

Column 8, line 40, should be

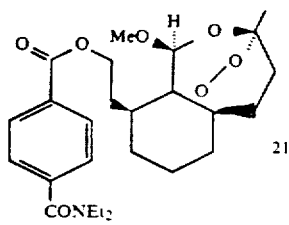

UNITED STATES PATENT AND TRADEMARK OFFICE
CERTIFICATE OF CORRECTION

PATENT NO. : 5,225,437
DATED : July 6, 1993
INVENTOR(S) : POSNER et al.

Page 7 of 21

It is certified that error appears in the above-indentified patent and that said Letters Patent is hereby corrected as shown below:

Column 8, line 63, should be

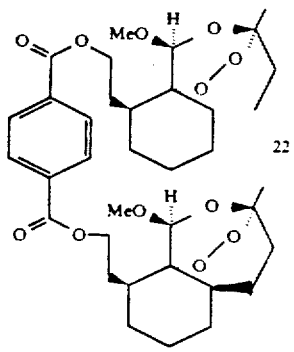

Column 9, line 5, should be

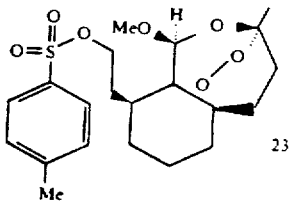

UNITED STATES PATENT AND TRADEMARK OFFICE
CERTIFICATE OF CORRECTION

PATENT NO. : 5,225,437
DATED : July 6, 1993
INVENTOR(S) : POSNER et al.

It is certified that error appears in the above-indentified patent and that said Letters Patent is hereby corrected as shown below:

Column 9, line 18, should be

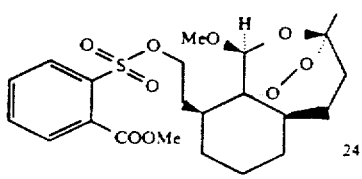

Column 9, line 30, should be

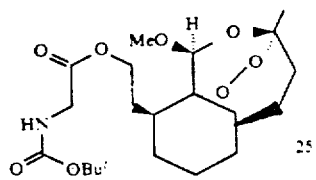

UNITED STATES PATENT AND TRADEMARK OFFICE
CERTIFICATE OF CORRECTION

PATENT NO. : 5,225,437
DATED : July 6, 1993
INVENTOR(S) : POSNER et al.

It is certified that error appears in the above-indentified patent and that said Letters Patent is hereby corrected as shown below:

Column 9, line 40, should be

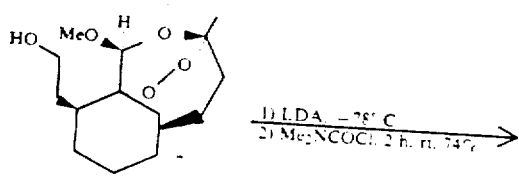

Column 9, line 45, should be

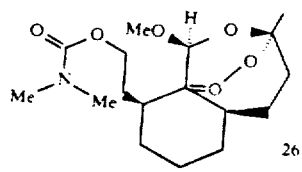

UNITED STATES PATENT AND TRADEMARK OFFICE
CERTIFICATE OF CORRECTION

PATENT NO. : 5,225,437
DATED : July 6, 1993
INVENTOR(S) : POSNER et al.

It is certified that error appears in the above-indentified patent and that said Letters Patent is hereby corrected as shown below:

Column 9, line 63, should be

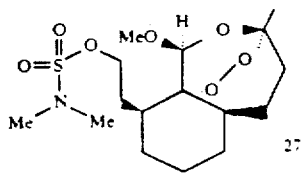

Column 10, line 5, should be

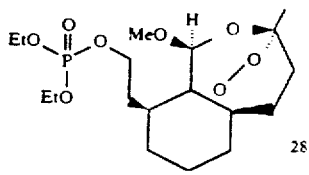

UNITED STATES PATENT AND TRADEMARK OFFICE
CERTIFICATE OF CORRECTION

PATENT NO. : 5,225,437
DATED : July 6, 1993
INVENTOR(S) : POSNER et al.

Page 11 of 21

It is certified that error appears in the above-indentified patent and that said Letters Patent is hereby corrected as shown below:

Column 10, line 28, should be

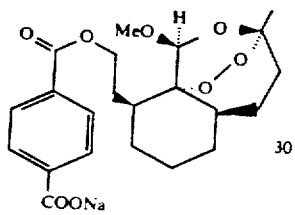

Column 10, line 35, should be

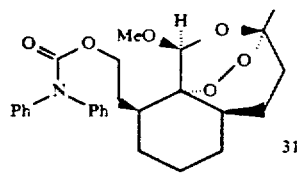

UNITED STATES PATENT AND TRADEMARK OFFICE
CERTIFICATE OF CORRECTION

PATENT NO. : 5,225,437
DATED : July 6, 1993
INVENTOR(S) : POSNER et al.

It is certified that error appears in the above-indentified patent and that said Letters Patent is hereby corrected as shown below:

Column 11, line 18, should be

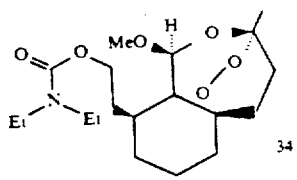

Column 11, line 32, should be

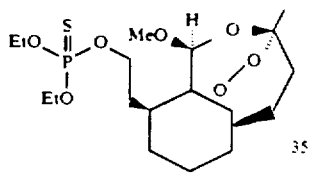

UNITED STATES PATENT AND TRADEMARK OFFICE
CERTIFICATE OF CORRECTION

PATENT NO. : 5,225,437
DATED : July 6, 1993
INVENTOR(S) : POSNER et al.

It is certified that error appears in the above-indentified patent and that said Letters Patent is hereby corrected as shown below:

Column 11, line 40, should be

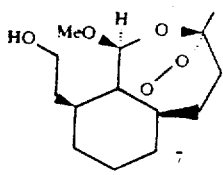

Column 11, line 48, should be

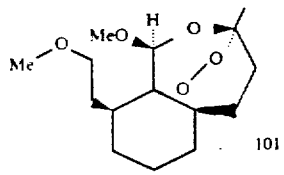

UNITED STATES PATENT AND TRADEMARK OFFICE
CERTIFICATE OF CORRECTION

PATENT NO. : 5,225,437
DATED : July 6, 1993
INVENTOR(S) : POSNER et al.

It is certified that error appears in the above-indentified patent and that said Letters Patent is hereby corrected as shown below:

Column 11, line 60, should be

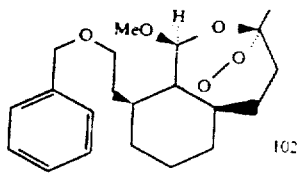

Column 12, line 5, should be

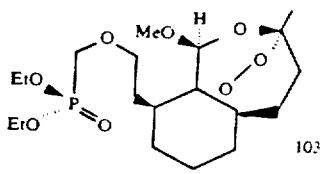

UNITED STATES PATENT AND TRADEMARK OFFICE
CERTIFICATE OF CORRECTION

PATENT NO. : 5,225,437
DATED : July 6, 1993
INVENTOR(S) : POSNER et al.

It is certified that error appears in the above-indentified patent and that said Letters Patent is hereby corrected as shown below:

Column 12, line 18, should be

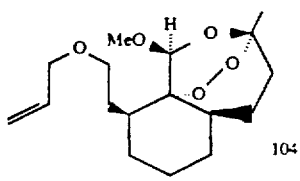

Column 12, line 35, should be

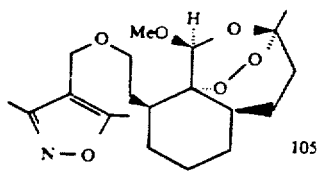

UNITED STATES PATENT AND TRADEMARK OFFICE
CERTIFICATE OF CORRECTION

PATENT NO. : 5,225,437
DATED : July 6, 1993
INVENTOR(S) : POSNER et al.

It is certified that error appears in the above-indentified patent and that said Letters Patent is hereby corrected as shown below:

Column 12, line 45, should be

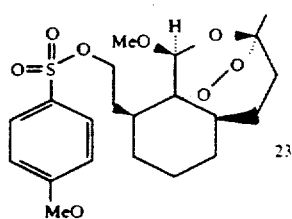

Column 12, line 55, should be

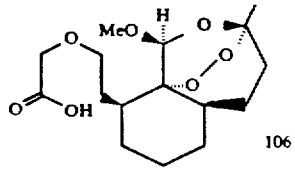

UNITED STATES PATENT AND TRADEMARK OFFICE
CERTIFICATE OF CORRECTION

PATENT NO. : 5,225,437
DATED : July 6, 1993
INVENTOR(S) : POSNER et al.

It is certified that error appears in the above-indentified patent and that said Letters Patent is hereby corrected as shown below:

Column 12, line 65, should be

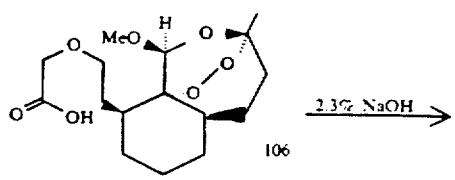

Column 13, line 5, should be

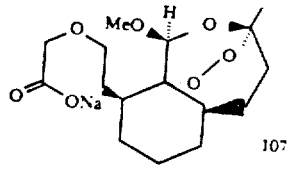

UNITED STATES PATENT AND TRADEMARK OFFICE
CERTIFICATE OF CORRECTION

PATENT NO. : 5,225,437
DATED : July 6, 1993
INVENTOR(S) : POSNER et al.

Page 18 of 21

It is certified that error appears in the above-indentified patent and that said Letters Patent is hereby corrected as shown below:

Column 13, line 15, should be

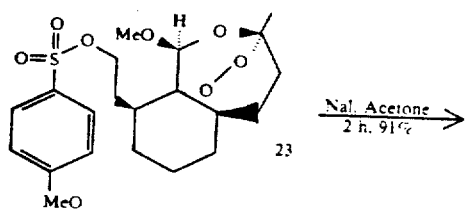

Column 13, line 23, should be

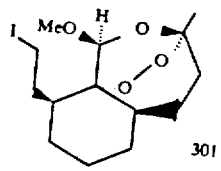

UNITED STATES PATENT AND TRADEMARK OFFICE
CERTIFICATE OF CORRECTION

PATENT NO. : 5,225,437
DATED : July 6, 1993
INVENTOR(S) : POSNER et al.

It is certified that error appears in the above-indentified patent and that said Letters Patent is hereby corrected as shown below:

Column 28, line 12, should be

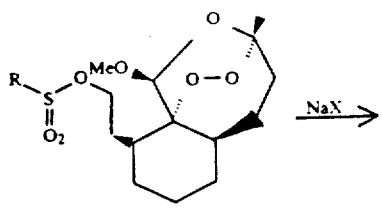

Column 28, line 20, should be

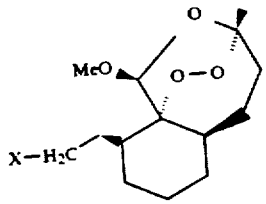

UNITED STATES PATENT AND TRADEMARK OFFICE
CERTIFICATE OF CORRECTION

PATENT NO. : 5,225,437
DATED : July 6, 1993
INVENTOR(S) : POSNER et al.

It is certified that error appears in the above-indentified patent and that said Letters Patent is hereby corrected as shown below:

Column 29, line 7, should be

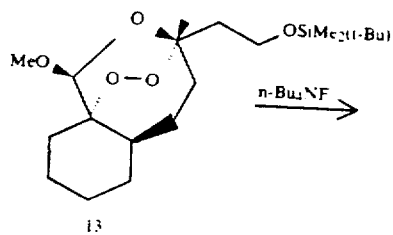

Column 29, line 17, should be

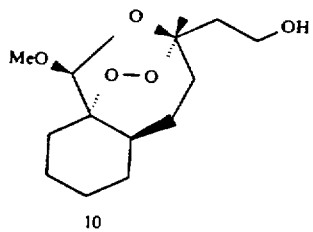

UNITED STATES PATENT AND TRADEMARK OFFICE
CERTIFICATE OF CORRECTION

PATENT NO. : 5,225,437
DATED : July 6, 1993
INVENTOR(S) : POSNER et al.

It is certified that error appears in the above-indentified patent and that said Letters Patent is hereby corrected as shown below:

Column 36, line 25, should be

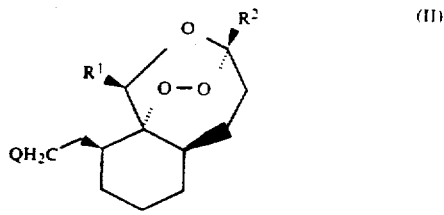

Structure (a) of the equation bridging columns 31 and 32 delete "MaO" and replace with --MeO--.

The symbol "Sl" in the equation bridging columns 31 and 32 and in both equations in column 33 should be --Si--.

Signed and Sealed this

Thirty-first Day of May, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.   : 5,225,437
DATED        : July 6, 1993
INVENTOR(S)  : POSNER ET AL It is certified that error appears in the above-identified patent and that said Letters Patent is hereby corrected as shown below:

At Col. 1, line 4, insert:

The work that resulted in the subject invention was supported by the National Institutes of Health under Grant No. AI 34885.

Signed and Sealed this

Twenty-second Day of September, 1998

Attest:

BRUCE LEHMAN

Attesting Officer

Commissioner of Patents and Trademarks